United States Patent [19]
Romeo et al.

[11] Patent Number: 5,677,285
[45] Date of Patent: Oct. 14, 1997

[54] DERIVATIVES OF NEURAMINIC ACID

[75] Inventors: Aurelio Romeo, Rome; Gunter Kirschner, Abano Terme, both of Italy; Hari Manev, Pittsburgh, Pa.; Martino Trimarco; Gino Toffano, both of Padua, Italy

[73] Assignee: Fidia S.P.A., Abano Terme, Italy

[21] Appl. No.: 379,602

[22] PCT Filed: Aug. 3, 1993

[86] PCT No.: PCT/US93/07307

§ 371 Date: Apr. 26, 1995

§ 102(e) Date: Apr. 26, 1995

[87] PCT Pub. No.: WO94/03469

PCT Pub. Date: Feb. 17, 1994

[30] Foreign Application Priority Data

Aug. 3, 1992 [IT] Italy .................. PD92A0146

[51] Int. Cl.$^6$ .......... A61K 31/70; A61K 38/16; A61K 38/14; C07H 15/00
[52] U.S. Cl. .......... 514/25; 530/322; 536/17.2; 536/17.3; 536/17.4; 536/17.5; 536/17.6; 536/17.9; 536/18.4; 536/18.7; 536/53; 536/54; 536/55; 514/8; 514/24; 514/27; 514/32; 514/35
[58] Field of Search .......... 530/322; 536/17.2, 536/17.3, 17.4, 17.5, 17.6, 17.9, 18.4, 18.7, 53, 54, 55; 514/8, 24, 25, 27, 32, 35

[56] References Cited
PUBLICATIONS

Olney *Annu. Rev. Pharmacol. Toxicol.* 1990, 30, 47–71.
Schmid et al. *Liebigs Ann. Chem.* 1986, 2104–2111.
Holmquist *Acta Chemica Scandinavica B* 1974, 28(9), 1065–1068.
Eschenfelder et al. *Hoppe–Seyler's Z. Physiol, Chem.* 1983, 364, 1411–1417.
von Itzstein et al. Nature (Jun. 1993) Rational design of potent sialidase–based inhibitors of influenza virus replication, pp. 418–423.

*Primary Examiner*—Kathleen K. Fonda
*Attorney, Agent, or Firm*—Birch, Stewart, Kolasch & Birch, LLP

[57] ABSTRACT

Provided are new derivatives of neuraminic acid of formula (I), where Ac represents an acyl residue of an aliphatic, araliphatic, aromatic, alicyclic, or heterocyclic carboxylic acid, including carboxylic amides, their 2-hydrocarbyl-glycosides, and their peracylated derivatives at the hydroxy groups of both these series of amides. These compositions are therapeutically useful in providing a protective effect against the neurotoxicity induced by excitatory amino acids, and can therefore be used in therapies of the central nervous system.

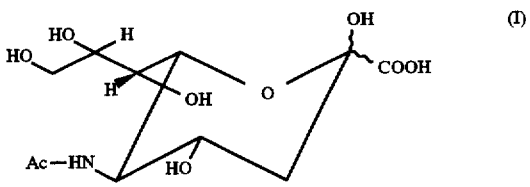

50 Claims, No Drawings

DERIVATIVES OF NEURAMINIC ACID

This is the U.S. national stage entry of PCT/US93/07307, filed Aug. 3, 1993.

BACKGROUND OF THE INVENTION

1. Field of the Invention

The present invention relates to new derivatives of neuraminic acid, especially carboxylic amides of the following formula, $$\text{(I)}$$

where Ac represents an acyl residue of a carboxylic acid of the aliphatic, araliphatic, aromatic, alicyclic or heterocyclic series, comprising the carboxylic amides, their 2-hydrocarbyl-glycosides, and their peracylated derivatives at the hydroxy groups of both these series of amides.

These compounds have interesting pharmacological properties, especially a protective effect against the neurotoxicity induced by excitatory amino acids of the of glutamic acid type, and can therefore be used in therapies of the central nervous system, such as those following cerebral degenerations or lesions, e.g., ischemia, hypoxia, epilepsy, trauma or compressions, metabolic dysfunctions, aging, toxic-infective and chronic neurodegenerative diseases, like Alzheimer's, Parkinson's, and Huntington's diseases.

The carboxylic amides and their derivatives of formula I according the present invention are new.

2. Description of Related Art

In the literature, there is a description of the non-substituted amide of N-acetyl-neuraminic acid, prepared as an intermediate in the synthesis of tetrazolyl-2-decarboxy-N-acetyl-neuraminic acid (see Ann. 1986, 2104–11).

In an article published in Hoppe Seyler's Physiol. Chemie, 1983, 364 (109) 1411–17, there is a description of the amides obtainable through the reaction of the benzylketoside of N-acetyl-neuraminic acid with L-glycine, L-glutamic acid, and L-phenylalanine, followed by the elimination of the benzyl group through catalytic hydrogenation; no pharmacological action is described for these derivatives.

SUMMARY OF THE INVENTION

In addition to providing new derivatives of neuraminic acid, the present invention also provides pharmacological preparations containing the aforesaid derivatives for therapeutic use.

A third object of the present invention concerns the therapeutic use of these preparations.

A final object of the present invention concerns procedures for the production of these new derivatives.

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are incorporated by reference in their entirety.

The amides and their derivatives according to the present invention can derive from both possible anomeric forms in position 2 of neuraminic acid, and therefore all the new compounds can be of either type at that position. The steric configuration of the other carbon atoms of the neuraminic residue is the same as that of the natural acid.

The acyl group Ac on the nitrogen of the neuraminic acid residue in the aforesaid formula has at least 4 and not more than 24 carbon atoms, and derives from non-substituted or substituted acids, preferably from 1 to 3 functions selected from the group consisting of halogen atoms; free, esterified, or etherified hydroxylic or mercapto groups; free or esterified carboxylic or sulfonic groups, or such groups transformed into amides; and free hydrocarbylic groups or hydrocarbylic groups substituted aminic groups.

These acids can be interrupted by —SO—, —SO$_2$—, or phenylene groups in the carbon atom chain of the hydrocarbylic residue. The halogen atoms are preferentially fluorine, bromine, or chlorine. Esterified hydroxylic or mercapto groups can derive from one of the acids mentioned regarding the Ac group, but they preferentially derive from aliphatic or aromatic acids with not more than 8 carbon atoms. Moreover, they can derive from inorganic acids such as, for example, sulfuric or phosphoric acid, or especially from their partial esters with mono- or polyvalent aliphatic alcohols, eventually with hydroxylic groups or aminic functions substituting in the hyrdocarbylic residues. Finally, they can derive from hydrocarbylsulfonic acids.

Etherified hydroxy or mercapto groups, or esterified carboxylic or sulfonic groups, preferentially derive from alcohols of the aliphatic series having no more than 8 carbon atoms, or from the araliphatic series with only one benzene ring and an alkylene of 1 or 2 carbon atoms. The hydrocarbylic groups which can substitute the aminic groups preferentially derive from these alcohols; the amino groups can also be in the form of quaternary ammonium salts, e.g., tetraalkyl groups, e.g., tetrabutylammonium.

Ac groups containing functionally modified hydroxy, mercapto, or amino groups can also be present in the form of hydrocarbylic residues of the Ac acyl group, interrupted in the carbon atom chain by the heteroatoms —O—, —S—, or —NH—, and, in the particular case of esters of hydroxy or mercapto groups with partially esterified sulfuric or phosphoric acid, by groups of the type $$-O-S-O-, \quad -O-P\begin{matrix}O-\\ \diagdown\\ OH\end{matrix}, \quad \text{or} \quad -O-P\begin{matrix}O-\\ \diagdown\\ O^-\end{matrix}$$

and in those of esters with hydrocarbylsulfonic acids (e.g., p-toluenesulfonic or methanesulfonic acid), by —O—SO$_2$.

The hydrocarbylic residue Ac, as already stated, can be blocked by sulfoxide or sulfonyl residues. In amides, converted carboxylic or sulfonic groups preferentially derive from lower aliphatic amines with not more than 4 carbon atoms, or from araliphatic amines with only one benzene ring and one or two carbon atoms in alkenyl residue.

The acids from which the Ac groups of the aliphatic series derive can he saturated or unsaturated, and in this case, they preferentially have only one double bond, and can have linear or branched chains. Of particular interest are the following acids: butyric, valeric, particularly normal valeric and isovaleric, trimethylacetic (pivalic acid), caproic, isocaproic, enantic, caprylic, pelargonic, capric, undecilic, di-tert-butyl-acetic, 2-propyl-valeric (valproic acid), lauric, tridecilic, myristic, pentadecilic, palmitic, margaric, stearic, arachic, behenic, and lignoceric.

Among substituted aliphatic acids, levulinic acid must be mentioned; among dicarboxylic acids, succinic acid; and among natural amino acids, e.g., valine, leucine, phenylalanine, tryptophan, aminobutyric acid, methionine, lysine, aspartic acid, glutamic acid, proline, hydroxyproline; among the acids substituted with halogens, mono- and dichloroacetic acid, trichlorobutyric acid, and dibromobutyric acid.

The Ac group of formula I can also derive from natural or synthetic peptides preferentially having not more than 12 amino acids, selected from naturally occurring amino acids, e.g., those aforesaid.

Of particular interest according to the present invention are those in which Ac is an acyl residue belonging to peptides of the thymus gland. Acids, from which derive an Ac group of araliphatic nature, are e.g., phenylacetic, cinnamic, phenylpropionic or atropic acid. Among aromatic acids, benzoic acid and its methylated homologues, salicylic acid, anthranilic acid, trimethoxybenzoic acid, phthalic or terephthalic acid, O,O'-dicarbonic acid, chlorobenzoic acid, vanillic acid, and veriatric or piperonilic acid must be mentioned.

Among Ac acyl groups belonging to acids of the alicyclic series, there must be mentioned cyclohexane- and cyclopentane-carbonic acids, hexahydrophthalic, hexahydroisophhtalic and hexahydroterephhtalic acids, camphoric and apocamphoric acid, and, among acids with a higher carbon atom content, prostaglandins and steroidic acids such as, for example, cholanic or cholic acid.

If Ac represents an acyl group belonging to an acid of the heterocyclic series, this can be one of the following acids: nicotinic or isonicotinic, cinconninic, lysergic, isolysergic, dihydrolysergic, 2-bromo-lysergic, 2-bromo-dihydrolysergic, 1-methyl-lysergic, 1-methyl-dihydro-lysergic, 1-methyl-2-bromo-lysergic or theophyllinacetic.

The carboxylamido functions according to the present invention can derive from ammonia (and in this case it is the non-substituted amide, —$CONH_2$), or from primary or secondary aliphatic, aromatic, araliphatic, alicyclic or heterocyclic amines, which can also be substituted in the hydrocarbylic residue by one to three functions selected from the group consisting of free, esterified, or etherified hydroxylic or mercapto groups, halogens, free, esterified, or amide-modified carboxylic or sulfonic groups, and free or hydrocarbyl-substituted amino groups, wherein the hydrocarbyl group is blocked with an —SO— or —$SO_2$— group. These amines have no more than 24 carbon atoms.

The functions which can eventually substitute the carbon atom chain of the amide or the amine are preferentially those mentioned for the Ac group of formula I. Aliphatic amines can have an open, saturated, unsaturated, linear, branched or cyclic chain. Of particular interest are alkyl- and dialkylamines having from 1 to 12 carbon atoms, such as, for example, methylamine, ethylamine, propylamine, hexylamine, diethylamine, dimethylamine, diisopropylamine, dihexylamine and alkylenylamines having from 3 to 6 cyclic carbon atoms, wherein the rings are substituted or non-substituted, preferentially between one and three C1–14 alkyl groups, e.g., methyl groups, like pyrrolidine, piperidine, and azepine.

The hydrocarbylic chains can also be blocked with heteroatoms such as, for example, —O—, —S—, or —NH— groups, or they can be substituted, as already mentioned, with different functions, particularly alcoholic, amino, mercapto, carboxylic, and sulfonic functions, or by their functionally modified forms, such as esters, ethers, or alkylated derivatives. Of particular interest are the following: aliphatic diamines, like ethylenediamine, trimethylenediamine, tetramethylenediamine, penta- and hexamethylenediamine, piperazine and its N-alkyl or C-alkyl derivatives having a C1–4 alkyl; aminoalcohols like aminoethanol or aminopropanol; aminomercaptanes like mercaptoethylamine; aliphatic aminoacids like all those mentioned for the Ac group of formula I; and aminosulfonic acids like taurine. Moreover, morpholine and thiomorpholine and their alkylated derivatives such as, for example, those which are N- or C-methylated, are also useful.

The amide groups eventually can derive from peptides, such as those mentioned for the Ac group.

Of particular interest also are some derivatives of amines having a large number of carbon atoms of an aliphatic nature, and which are related to phospholipids or sphingolipids or similar derivatives.

According to the present invention, the carboxylic group of the N-acyl-neuraminic acids can contain saturated or unsaturated aminic groups having between 14 and 24 carbon atoms, or bases present in the following lipids: phosphatidylethanolamine, phosphatidylserine, sphingosine, dihydrosphingosine, psychosine, dihydropsychosine, phosphorylcholine-sphingosine, phosphorylcholine-dihydrosphingosine, and phytosphingosine.

The carboxylamides of the present invention can also derive from aromatic or araliphatic amines, but preferentially from those having only one aromatic ring, which can be substituted with 1 to 3 functional groups selected from the group consisting of halogens, hydroxylic or methoxylic groups, carboxylic or sulfonic groups, or C1–4 lower aliphatic hydrocarbylic groups such as, for example, aniline, anthranilic acid, 1-amino-4-sulfonic acid, and benzylamide. In the aforesaid aliphatic amines, in one or more positions of the hydrocarbylic chain, a phenyl group can be present to block the carbon atom chain.

Amines which can be used for the conversion into amides according to the present invention include, for example, amines of pyrimidines such as cyanmethine, i.e., 2,4-dimethyl-6-amino-pyrimidine, purine derivatives such as adenine, 4-aminouracil, and guanine, and alkaloids such as ephedrine, tyramine, and adrenalin.

The 2-hydrocarbyl-glycosides of the aforesaid amides of neuraminic acids of formula I derive from alcohols of the aliphatic, cycloaliphatic, aromatic, araliphatic or heterocyclic series, particularly from alcohols of the aliphatic series having not more than 12 carbon atoms, or from the araliphatic series having preferentially only one benzene ring, eventually substituted with 1–3 lower C1–4 alkyl groups, for example methyl groups, and not more than 4 carbon atoms in the aliphatic chain, or from alcohols of the alicyclic or aliphatic-alicyclic series having only one cycloaliphatic ring and not more than 14 carbon atoms, or from the heterocyclic series having not more than 12, and especially 6 carbon atoms, and only one heterocyclic ring containing 1 or 2 heteroatoms selected from the group consisting of —NH—, —O— and —S—. These alcohols can also be substituted, particularly with functions selected from the group consisting of hydroxy, amino, and alkoxy groups having not more than 4 carbon atoms, and carboxylic and carbalkoxy groups having not more than 4 carbon atoms in the alkyl residues.

The aforesaid alcohols can be mono- and polyvalent, particularly bivalent. Among alcohols of the aliphatic series, of particular interest are lower alcohols having not more than 6 carbon atoms such as, for example, methyl, ethyl, propyl, isopropyl, n-butyl, isobutyl, and tert-butyl alcohol, and ethyleneglycol and propyleneglycol, among divalent alcohols. Among alcohols of the araliphatic series, of particular interest are those having only one benzene residue, like benzyl and phenetyl alcohol; among alcohols of the alicyclic series, preferred are those having only one cycloaliphatic ring, like cyclohexylic alcohol. Among alcohols of the alicyclic series having more rings, steroid alcohols such as, for example, those of the pregnane group, like corticosteroids, and among these methylprednisolone, must be mentioned. Among alcohols of the heterocyclic series there must be mentioned tetrahydrofuranol, tetrahydropyranol, furfuryl alcohol and pyridylcarbinol.

In peracylated derivatives of the amides and their 2-hydrocarbyl-glycosides, the hydroxy groups in position 2,4,7,8 and 9 are acylated with acids belonging to the aliphatic, aromatic, araliphatic, alicyclic and heterocyclic series. Peracylated derivatives derive preferentially from acids of the aliphatic series having not more than 10 carbon atoms, like formic, acetic, and butyric acid and their isomers; valeric acids, like normal valeric, or pivalic acid; and capronic or capric acid. These acids can also be substituted, and the peracylated derivatives can therefore derive from hydroxyacids like lactic acid, from amino acids like glycine, or from dibasic acids like succinic, malonic or maleic acid. Among aromatic acids, there must be mentioned those with only one benzene ring, particularly benzoic acid and its derivatives with methyl, hydroxy, amino or carboxylic groups such as, for example, p-aminobenzoic, salicylic and phthalic acid.

The new compounds according to present invention can eventually be transformed into their acidic addition salts or into metallic salts with organic bases, if the corresponding basic or acidic functions are present. These salts can also be used for the therapeutic purposes described infra. With resepect to this equivalence between salts and amides in free form, it is obvious that what will be described for the compounds in free form, especially their pharmaceutical and medical applications, is also true for the corresponding salts, provided that these salts are therapeutically acceptable, and therefore they also form an object of the present invention. These salts can also be used for the purification of the amides, and in this case also, therapeutically non-acceptable bases and acids can be used, such as salts of picric and picrolonic acid.

Compounds of the Present Invention

Defined compounds according to the present invention include the amide, methylamide, ethylamide, dimethylamide, diethylamide, propylamide, glycine amide, L-serine amide, aminobutyric amide, L-cysteine amide, taurine amide, the amide of cysteic acid, homocysteic acid, N-palmitoyl-neuraminic acid, N-stearoyl-neuraminic acid, N-acetyl-neuraminic acid, N-propionyl-neuraminic acid, N-pivaloyl-neuraminic acid, N-valeroyl-neuraminic acid, N-caproyl-neuraminic acid, N-lauroyl-neuraminic acid, N-succinyl-neuraminic acid, phenylacetyl-neuraminic acid, benzoyl-neuraminic acid, trimethoxy-benzoyl-neuraminic acid, phthaloyl-neuraminic acid, chlorobenzoyl-neuraminic acid, vanilloyl-neuraminic acid, cyclopenthane- and cyclohexane-carbonyl-neuraminic acid, N-nicotinyl-neuraminic acid, N-isonicotinyl-neuraminic acid, lisergyl-neuraminic acid, 2-bromo-lisergyl-neuraminic acid, 1-methyl-lisergyl-neuraminic acid, theophillineacetyl-neuraminic acid, and their 2-glycosides derived from one of the following alcohols: methyl alcohol, ethyl alcohol, propyl alcohol, isopropyl alcohol, butyl alcohol, isobutyl alcohol, tertbutyl alcohol, ethyleneglycol, propyleneglycol, benzyl alcohol, methylprednisolone, tetrhydrofuranol, tetrahydropyranol, furfuryl alcohol, and pyridylcarbinol.

Other compounds of the present invention include the amide, methylamide, ethylamide, dimethylamide, diethylamide, propylamide, glycine amide, L-serine amide, aminobutyric amide, L-cysteine amide, taurine amide of N-acylneuraminic acids having an acyl group deriving from one of the following acids: aminobutyric, methionine, lysine, aspartic acid, glutamic acid, proline, tryptophan, or from an acyl residue deriving from a peptide present in the thymus, and their 2-glycosides deriving from one of the following alcohols: methyl alcohol, ethyl alcohol, propyl alcohol, isopropyl alcohol, butyl alcohol, isobutyl alcohol, tertbutyl alcohol, ethyleneglycol, propyleneglycol, benzyl alcohol, methyl-prednisolone, tetrahydrofuranol, tetrahydropyranol, furfuryl alcohol, and pyridylcarbinol.

Another group of interesting compounds according to the present invention is formed by the amides deriving from pyrrolidine, piperidine, azepine, ethylenediamine, trimethylenediamine, hexamethylenediamine, piperazine or N-methyl or N-ethyl-piperazine, aminoethanol, aminopropanol, mercaptoethylamine, morpholine, tiomorpholine, or peptides like those present in the thymus, and from phosphatidylethanolamine, phosphatidylserine, sphingosine, psychosine, dihydropsychosine, sphingosylphosphorylcholine, dihydrosphingosylphosphorylcholine, or from the phytosphingosine of one of the following N-acyl-neuraminic acids: N-palmitoyl-neuraminic acid, N-stearoyl-neuraminic acid, N-acetyl-neuraminic acid, N-propionyl-neuraminic acid, N-pivaloyl-neuraminic acid, N-valeroyl-neuraminic acid, N-caproyl-neuraminic acid, N-lauroyl-neuraminic acid, N-succinyl-neuraminic acid, phenylacetyl-neuraminic acid, phthaloyl-neuraminic acid, chlorobenzoyl-neuraminic acid, N-nicotinyl-neuraminic acid, N-isonicotinyl-neuraminic acid, lisergyl-neuraminic acid, 2-bromo-lisergyl-neuraminic acid, 1-methyl-lisergyl-neuraminic acid, theophillineacetyl-neuraminic acid, and their 2-glycosides derived from one of the following alcohols: methyl alcohol, ethyl alcohol, propyl alcohol, isopropyl alcohol, butyl alcohol, isobutyl alcohol, tertbutyl alcohol, ethyleneglycol, propyleneglycol, benzyl alcohol, methylprednisolone, tetrhydrofuranol, tetrahydropyranol, furfuryl alcohol, and pyridylcarbinol.

Other derivatives are those peracylated at the hydroxy groups of N-acyl-neuraminic acid, and particularly peracetates, perpropionates, perbutyrates, pervalerianates, perpivalates, persuccinates and perbenzoates.

Synthesis of the Compounds of the Present Invention

The present invention also comprises processes for the preparation of the new amides of N-acyl-neuraminic acids, their 2-hydrocarbylglycosides, and their salts.

These processes are already known, and consist of the stepwise introduction of the amine function and eventually of the 2-glycosidic group into an N-acyl-neuraminic acid, and eventually of acyl groups into the hydroxy groups and the final formation of their salts.

In a preferred embodiment, the carboxylic group of an N-acyl-neuraminic acid, in which the acyl group is desired in the final compound, or its 2-hydrocarbyl-glycosidic derivatives, is transformed to an amide group and, if desired, the 2-hydrocarbyl group can be eliminated, again forming the hydroxy group; if desired, the obtained compound is converted into a peracylated derivative at the hydroxy functions.

The carboxy group of the neuraminic acid can be converted into the amide, and eventually the 2-hydroxy group in its hydrocarbyl derivatives in both sequences and acylate the free amino group with the desired acid and, if desired, peracylate the free hydroxy groups, or perform this peracylation in every step of the processes, e.g., at the beginning.

The conversion of the carboxylic group of N-acyl derivatives of neuraminic acid or of their 2-hydrocarbyl-glycosides to the corresponding amide can be performed directly starting from the acid, or from its metal or organic base salt, or indirectly preparing first the ester of the acid, an anhydride, or a halogenide of the acid, and then converting these compounds into the amide.

A preferred method consists of activating the carboxylic group and then reacting the intermediate with the desired amine, utilizing methods known in peptide chemistry, avoiding methods utilizing acidic or basic conditions. If metal salts of the acid, like sodium, are used, it is convenient to treat the salt with an ion exchange resin of the Dowex type or a similar resin. As an example, it is possible to use the condensation method in presence of carbodiimides, e.g., dicyclohexylcarbodiimide, benzylisopropylcarbodiimide or benzylethylcarbodiimide, in the presence of 1-hydroxybenzo-triazol, or the condensation in the presence of N,N'carbonyl-diimidazol. Starting from the aforesaid acidic derivatives, like esters or halogenides, e.g., bromides or chlorides, the transformation into the amide is carried out by direct treatment with the desired amine at relatively low temperature, e.g., room temperature or −5° C. to 10° C., or higher temperatures, e.g., between 30° and 120° C. Ketones, aromatic hydrocarbides, dimethylformamide, dimethylsulfoxide, dioxane or tetrahydrofuran can be used as solvents. The starting esters can be aliphatic esters, e.g., ethyl or methyl esters, or aromatic esters, e.g., phenols.

The 2-O-hydrocarbyl derivatives of the starting compounds or of the compounds already possessing the amine function are prepared according to the conditions known for the acetylation of aldehydes or ketones, or for the preparation of glycosides. The 2-hydrocarbyl groups of the glycosides can be transformed at the hydroxy group at every step by hydrolysis with acids under mild conditions.

If acylation of the amine group of neuraminic acid is performed at the end of the procedure, e.g., after amide or glycoside formation, known acylation methods are used, e.g., treatment of the compound with acid halogenides or anhydrides, eventually in the presence of inorganic or organic bases, like pyridine or collidine. This acylation can be performed contemporaneously with the acylation of hydroxy groups.

The transformation of the final compounds into their salts, as well as the interconversion of the salts, is performed in a known manner, as for example when intermediate salts are prepared for their purification.

The aforesaid procedure according to the present invention also comprises all variations in which the procedure is stopped at every step, or in which the starting compound is an intermediate, or in which the starting compounds are prepared in situ.

The synthesis of the compounds of the present invention is illustrated by the following examples.

EXAMPLE 1

Butilamide of N-acetylneuraminic acid 3.23 g (10 mM) of N-acetylneuraminic acid methylester, prepared according to Kuhn et al., Chem Ber. 99,611 (1966), were solubilized in 50 ml of anhydrous methyl alcohol; 3.66 g (50 mM) of 2-butylamine were added. The mixture was stirred for 5 hours at 40° C. The solution was evaporated under vacuum and the residue was purified by silica gel chromatography, using as solvent a mixture of methylene chloride/methyl alcohol/water, 110:40:6. The fractions containing the butilamide of N-acetyl-neuraminic acid were gathered and evaporated under vacuum. The residue was crystallized from 50 ml of n-propyl alcohol. Yield: 85%.

Rf=0.25, chloroform/methyl alcohol/water, 110:40:6.

EXAMPLE 2

β-2-O-ethylglycoside of butilamide of N-acetylneuraminic acid 3.65 g (10 mM) of the β-2-O-ethylglycoside of N-acetylneuraminic acid ethyl ester, prepared according to Kuhn et al., Chem Ber. 99, 611 (1966), were solubilized in 80 ml of anhydrous methyl alcohol; 3.66 g (50 mM) of 2-butylamine were added. The mixture was stirred for 5 hours at 40° C. The solution was evaporated under vacuum and the residue was purified by silica gel chromatography, using as solvent a mixture of methylene chloride/methyl alcohol/water, 80:20:2. The fractions containing the β-2-O-ethylglycoside of the butilamide of N-acetyl-neuraminic acid were gathered and evaporated under vacuum. The residue was crystallized from 50 ml of n-propyl alcohol and 100 ml of ethyl ether. Yield: 70%.

Rf=0.37, chloroform/methyl alcohol/water, 10:40:6;

0.19, chloroform/methyl alcohol/2.5N $NH_4OH$, 0:20:2.

EXAMPLE 3

β-2-O-ethylglycoside of the benzylamide of N-acetylneuraminic acid 3.65 g (10 mM) of the β-2-O-ethylglycoside of N-acetylneuraminic acid ethyl ester, prepared according to Kuhn et al., Chem Ber. 99, 611 (1966), were solubilized in 50 ml of anhydrous methyl alcohol; 5.36 g (50 mM) of benzylamine were added. The mixture was stirred for 5 hours at 40° C. The solution was evaporated under vacuum and the residue was purified by silica gel chromatography, using as solvent a mixture of methylene chloride/methyl alcohol/water, 80:20:2. The fractions containing the β-2-O-ethylglycoside of the benzylamide of N-acetyl-neuraminic acid were gathered and evaporated under vacuum. The residue was crystallized from 50 ml of isopropyl alcohol. Yield: 65%.

Rf=0.50, chloroform/methyl alcohol/water, 110:40:6;

0.16, chloroform/methyl alcohol/2.5N $NH_4OH$, 80:20:2.

EXAMPLE 4

β-2-O-ethylglycoside of the dimethylaminopropylamide of N-acetylneuraminic acid 3.65 g (10 mM) of the β-2-O-ethylglycoside of N-acetylneuraminic acid ethyl ester were solubilized in 50 ml of anhydrous methyl alcohol; 10.2 g (100 mM) of dimethylaminopropylamine were added. The mixture was stirred overnight at 25 ° C. The solution was evaporated under vacuum and the residue was purified by silica gel chromatography, using as solvent a mixture of methylene chloride/methyl alcohol/2.5N NH$_4$OH, 55:45:10. The fractions containing the β-2-O-ethylglycoside of dimethylaminopropylamide of N-acetyl-neuraminic acid were gathered and evaporated under vacuum. The residue was dissolved in 50 ml of water. Yield: 75%.

Rf=0.19, chloroform/methyl alcohol/2.5N NH$_4$OH, 40:60:15.

EXAMPLE 5

β-2-O-ethylglycoside of the dimethylaminopropylamide of N-acetylneuraminic acid (maleic acid salt)

3.65 g (10 mM) of the β-2-O-ethylglycoside of N-acetylneuraminic acid ethyl ester were solubilized in 50 ml of anhydrous methyl alcohol; 10.2 g (100 mM) of dimethylaminopropylamine were added. The mixture was stirred overnight at 25° C. The solution was evaporated under vacuum and the residue was purified by silica gel chromatography, using as solvent a mixture of methylene chloride/methyl alcohol/2.5N NH$_4$OH, 55:45:10. The fractions containing the β-2-O-ethylglycoside of the dimethylaminopropylamide of N-acetyl-neuraminic acid were gathered and evaporated under vacuum. The residue was dissolved in 50 ml of water, a stoichiometric amount of maleic acid was added, and the material was lyophilized. Yield: 75%.

Rf=0.19, chloroform/methyl alcohol/2.5N NH$_4$OH, 40:60:15.

EXAMPLE 6

β-2-O-ethylglycoside of the dimethylamide of N-acetylneuraminic acid 3.65 g (10 mM) of the β-2-O-ethylglycoside of N-acetylneuraminic acid ethyl ester were solubilized in 50 ml of anhydrous methyl alcohol; 4.5 g (100 mM) of dimethylamine were added. The mixture was stirred overnight at 25° C. The solution was evaporated under vacuum and the residue was purified by silica gel chromatography, using as solvent a mixture of methylene chloride/methyl alcohol/water, 80:20:2. The fractions containing the β-2-O-ethylglycoside of the dimethylamide of N-acetyl-neuraminic acid were gathered and evaporated under vacuum. The residue was crystallized from 30 ml of methanol and 150 ml of ethyl ether. Yield: 80%.

Rf=0.38, chloroform/methyl alcohol/water, 110:40:6.

EXAMPLE 7

β-2-O-ethylglycoside of the dimethylaminopropylamide of N-palmitoylneuraminic acid 5.62 g (10 mM) of the β-2-O-ethylglycoside of N-palmitoylneuraminic acid ethyl ester were solubilized in 50 ml of anhydrous methyl alcohol; 10.2 g (100mM) of dimethylaminopropylamine were added. The mixture was stirred overnight at 25° C. The solution was evaporated under vacuum and the residue was purified by silica gel chromatography, using as solvent a mixture of methylene chloride/methyl alcohol/water, 110:40:6. The fractions containing the β-2-O-ethylglycoside of the dimethylaminopropylamide of N-palmitoyl-neuraminic acid were gathered and evaporated under vacuum. The residue was dissolved in 60 ml of water and lyophilized. Yield: 70%.

Rf=0.12, chloroform/methyl alcohol/2.5N NH$_4$OH, 80:20:2.

EXAMPLE 8

β-2-O-ethylglycoside of the dimethylaminopropylamide of N-palmitoylneuraminic acid (maleic acid salt)

5.62 g (10 mM) of the β-2-O-ethylglycoside of N-palmitoylneuraminic acid ethyl ester were solubilized in 50 ml of anhydrous methyl alcohol; 10.2 g (100 mM) of dimethylaminopropylamine were added. The mixture was stirred overnight at 25° C. The solution was evaporated under vacuum and the residue was purified by silica gel chromatography, using as solventt a mixture of methylene chloride/methyl alcohol/water, 110:40:6. The fractions containing the β-2-O-ethylglycoside of the dimethylaminopropylamide of N-palmitoyl-neuraminic acid were gathered and evaporated under vacuum. The residue was dissolved in 50 ml of water, a stoichiometric amount of maleic acid was added, and the material was lyophilized. Yield: 70%.

Rf=0.12, chloroform/methyl alcohol/2.5N NH$_4$OH, 0:60:15.

EXAMPLE 9

α-2-O-ethylglycoside of the dimethylaminopropylamide of N-palmitoylneuraminic acid 5.48 g (10 mM) of the α-2-O-ethylglycoside of N-palmitoylneuraminic acid ethyl ester were solubilized in 50 ml of anhydrous methyl alcohol; 10.2 g (100 mM) of dimethylaminopropylamine were added. The mixture was stirred overnight at 25° C. The solution was evaporated under vacuum and the residue was purified by silica gel chromatography, using as solvent a mixture of methylene chloride/methyl alcohol/water, 110:40:6. The fractions containing the α-2-O-ethylglycoside of the dimethylaminopropylamide of N-palmitoyl-neuraminic acid were gathered and evaporated under vacuum. The residue was dissolved in 60 ml of water and lyophilized. Yield: 70%.

Rf=0.40, chloroform/methyl alcohol/0.3% CaCl$_2$, 60:40:9.

EXAMPLE 10

α-2-O-ethylglycoside of the dimethylaminopropylamide of N-palmitoylneuraminic acid (maleic acid salt)

5.48 g (10 mM) of the α-2-O-ethylglycoside of N-palmitoylneuraminic acid ethyl ester were solubilized in 50 ml of anhydrous methyl alcohol; 10.2 g (100 mM) of dimethylaminopropylamine were added. The mixture was stirred overnight at 25° C. The solution was evaporated under vacuum and the residue was purified by silica gel chromatography, using as solvent a mixture of methylene chloride/methyl alcohol/water, 110:40:6. The fractions containing the α-2-O-ethylglycoside of the dimethylaminopropylamide of N-palmitoyl-neuraminic acid were gathered and evaporated under vacuum. The residue was dissolved in 50 ml of water, a stoichiometric amount of maleic acid was added, and the material was lyophilized. Yield: 70%.

Rf=0.40, chloroform/methyl alcohol/0.3% CaCl$_2$, 60:40:9.

EXAMPLE 11

β-2-O-ethylglycoside of the dimethylamide of N-palmitoylneuraminic acid 5.56 g (10 mM) of the α-2-O-ethylglycoside of N-palmitoyl-neuraminic acid, sodium salt, were dissolved in 50 ml of pyridine, and 2.3 g (20 mM) of pyridinium chloride and 4.12 g (20 mM) of N,N'dicyclohexyl-carbodiimide were added. The mixture was stirred for 2 hours at 25° C. 4.5 g (100 mM) of dimethylamine were added and the reaction was conducted overnight at 25° C. The solution was evaporated under vacuum and the residue was purified by silica gel chromatography, using as solvent a mixture of methylene chloride/methyl alcohol/water, 80:10:1. The fractions containing the β-2-O-ethylglycoside of the dimethylamide of N-palmitoyl-neuraminic acid were gathered and evaporated under vacuum. The residue was dissolved in 50 ml of acetone and precipitated in 20 volumes of hexane. Yield: 90%.

Rf=0.69, chloroform/methyl alcohol/water, 110:40:6.

EXAMPLE 12

α-2-O-ethylglycoside of the dimethylamide of N-palmitoylneuraminic acid 5.48 g (10 mM) of the α-2-O-ethylglycoside of N-palmitoylneuraminic acid ethyl ester were solubilized in 50 ml of anhydrous methyl alcohol; 4.5 g (100 mM) of dimethylamine were added. The mixture was stirred overnight at 25° C. The solution was evaporated under vacuum and the residue was purified by silica gel chromatography, using as solvent a mixture of methylene chloride/methyl alcohol/water, 80:10:1. The fractions containing the α-2-O-ethylglycoside of the dimethylamide of N-palmitoyl-neuraminic acid were gathered and evaporated under vacuum. The residue was dissolved in 50 ml of acetone and precipitated in 20 volumes of hexane. Yield: 90%.

Rf=0.69, chloroform/methyl alcohol/water, 110:40:6.

EXAMPLE 13

α-2-O-ethylglycoside of the butylamide of N-acetylneuraminic acid 3.65 g (10 mM) of the α-2-O-ethylglycoside of N-acetylneuraminic acid ethyl ester were solubilized in 50 ml of anhydrous methyl alcohol; 3.66 g (50 mM) of butylamine were added. The mixture was stirred overnight at 25° C. The solution was evaporated under vacuum and the residue was purified by silica gel chromatography, using as solvent a mixture of methylene chloride/methyl alcohol/water, 80:20:2. The fractions containing the α-2-O-ethylglycoside of the butylamide of N-acetyl-neuraminic acid were gathered and evaporated under vacuum. The residue was crystallized from 50 ml of methanol and 300 ml of ethyl ether. Yield: 75%.

Rf=0.55, chloroform/methyl alcohol/water, 110:40:6;

Rf=0.53, chloroform/methyl alcohol/2.5N NH$_4$OH, 40:60:15.

EXAMPLE 14

α-2-O-ethylglycoside of the dimethylaminopropylamide of N-acetylneuraminic acid 3.65 g (10 mM) of the α-2-O-ethylglycoside of N-acetylneuraminic acid ethyl ester were solubilized in 50 ml of anhydrous methyl alcohol; 10.2 g (100 mM) of dimethylaminopropylamine were added. The mixture was stirred overnight at 25° C. The solution was evaporated under vacuum and the residue was purified by silica gel chromatography, using as solvent a mixture of methylene chloride/methyl alcohol/2.5N NH$_4$OH, 55:45:10. The fractions containing the α-2-O-ethylglycoside of the dimethylaminopropylamide of N-acetyl-neuraminic acid were gathered and evaporated under vacuum. The residue was dissolved in 50 ml of water and lyophilized. Yield: 70%.

Rf=0.21, chloroform/methyl alcohol/2.5N NH$_4$OH, 40:60:15.

EXAMPLE 15

α-2-O-ethylglycoside of the dimethylaminopropylamide of N-acetylneuraminic acid (maleic acid salt)

3.65 g (10 mM) of the β-2-O-ethylglycoside of N-acetylneuraminic acid ethyl ester were solubilized in 50 ml of anhydrous methyl alcohol; 10.2 g (100 mM) of dimethylaminopropylamine were added. The mixture was stirred overnight at 25° C. The solution was evaporated under vacuum and the residue was purified by silica gel chromatography, using as solvent a mixture of methylene chloride/methyl alcohol/2.5N NH$_4$OH, 55:45:10. The fractions containing the α-2-O-ethylglycoside of the dimethylaminopropylamide of N-acetyl-neuraminic acid were gathered and evaporated under vacuum. The residue was dissolved in 50 ml of water, a stoichiometric amount of maleic acid was added, and the material was lyophilized. Yield: 70%.

Rf=0.21, chloroform/methyl alcohol/2.5N NH$_4$OH, 40:60:15.

EXAMPLE 16

α-2-O-ethylglycoside of N-acetylneuraminic acid amide with L-alanine-D-isoglutamine 3.65 g (10 mM) of the α-2-O-ethylglycoside of N-acetylneuraminic acid ethyl ester were solubilized in 40 ml of water, and 10 ml (10 mM) of NaOH were added. The solution was maintained at 25° C. for 30 minutes, neutralized with 1N HCl, and eluted with water from a column containing 30 ml of Dowex 50x8 resin, pyridinium form. The eluate was lyophilized and the residue was solubilized in 100 ml of anhydrous pyridine. 1.15 g (10 mM) of N-hydroxysuccinimide and 4.13 g (20 mM) of N,N'-dicyclohexylcarbodiimide were added at −10° C. After 15 minutes, the temperature was raised to 25° C., and the mixture was stirred for 5 hours. 5.14 g (15 mM) of L-alanine-D-isoglutamine benzyl ester hydrochloride (prepared according to Le Francier and Kusumoto) were added at 25° C. The mixture was stirred overnight and then evaporated under vacuum. The obtained residue was dissolved in 200 ml of a mixture of n-butanol/water/acetic acid, 4:1:1, and hydrogenated in an H$_2$ current in the presence of BaSO$_4$-supported palladium. After filtration, the solution was evaporated, and the residue was purified by silica gel chromatography, using as solvent a mixture of methylene chloride/methyl alcohol/water, 60:35:8. The fractions containing the α-2-O-ethylglycoside of N-acetyl-neuraminic acid amide with n-alanine-D-isoglutamine were gathered and evaporated under vacuum. The residue was dissolved in 200 ml of water and lyophilized. Yield: 60%.

Rf=0.56, chloroform/methyl alcohol/2.5N NH$_4$OH, 60:35:8;

Rf=0.18, chloroform/methyl alcohol/0.3% CaCl$_2$, 60:40:9.

EXAMPLE 17

Peracetylated β-2-O-ethylglycoside of N-palmitoyl-neuraminic acid amide with L-alanine-D-isoglutamine 5.56 g (10 mM) of the α-2-O-ethylglycoside of N-palmitoylneuraminic acid, sodium salt, were solubilized in 50 ml of anhydrous N,N'-dimethylformamide at 25° C.; 3.06 g (11 mM) of p-bromophenacyl bromide were added and the solution was stirred overnight. 18 ml of anhydrous pyridine and 10.2 g of acetic anhydride were added and stirring was conducted for 24 hours at 35° C. The solution was evaporated under vacuum and the residue was dissolved with 100 ml of water and extracted three times with 200 ml of methylene chloride. The organic phases were washed twice with 50 ml of water and then gathered, anhydrified with anhydrous sodium sulfate, and evaporated under vacuum. The obtained residue was solubilized in 50 ml of anhydrous N,N'-dimethylformamide at 25° C.; 2.64 g (20 mM) of sodium thiophenate were added and the mixture was stirred for 4 hours. The solution was evaporated under high vacuum. The residue was extracted three times with 200 ml of ethyl acetate, washed with 100 ml of cold 1N HCl and twice with 50 ml of water. The organic phases were anhydrified with anhydrous sodium sulfate, gathered, and evaporated under vacuum. The residue was dissolved in 30 ml of water and eluted with water from a column containing 30 ml of Dowex 50X8 resin, pyridinium form. The eluate was lyophilized and the residue was solubilized in 100 ml of anhydrous pyridine. 1.15 g (10 mM) of N-hydroxysuccinimide and 4.13 g (20 mM) of N,N'-dicyclohexylcarbodiimide were added at −10° C. After 15 minutes the temperature was raised to 25° C. and the mixture was stirred for 5 hours. 5.14 g (15 mM) of L-alanine-D-isoglutamine benzyl ester hydrochloride (prepared according to Le Francier and Kusumoto) were added at 25° C. The mixture was stirred overnight and then evaporated under vacuum. The obtained residue was dissolved in 200 ml of a mixture of N-butanol/water/acetic acid, 4:1:1, and hydrogenated in an H$_2$ current in the presence of BaSO$_4$-supported palladium. After filtration, the solution was evaporated, and the residue was purified by silica gel chromatography, using as solvent a mixture of methylene chloride/methyl alcohol/water, 60:35:8. The fractions containing the α-2-O-ethylglycoside of N-acetyl-neuraminic acid amide with L-alanine-D-isoglutamine were gathered and evaporated under vacuum. The residue was dissolved in 200 ml of water and lyophilized. Yield: 55%.

Rf=0.54, chloroform/methanol, 90:10.

EXAMPLE 18

β-2-O-ethlglycoside of N-acetylneuraminic acid amide with L-alanine-D-isoglutamine 3.59 g (10 mM) of the β-2-O-ethylglycoside of N-acetylneuraminic acid, sodium salt, prepared according to Eschenfelder and Brossmer, Hoppe Seyler's Z. Physiol. Chem. 360, 1253 (1979), were solubilized in 50 ml of anhydrous N,N'-dimethylformamide at 25° C.; 3.06 g (11 mM) of p-bromophenacyl bromide were added and the solution was stirred overnight. 18 ml of anhydrous pyridine and 10.2 g of acetic anhydride were added and stirring was conducted for 24 hours at 35° C. The solution was evaporated under vacuum and the residue was dissolved with 100 ml of water and extracted three times with 200 ml of methylene chloride. The organic phases were washed twice with 50 ml of water and then gathered, anhydrified with anhydrous sodium sulfate, and evaporated under vacuum. The obtained residue was solubilized in 50 ml of anhydrous N,N'-dimethylformamide at 25° C.; 2.64 g (20 mM) of sodium thiophenate were added aid the mixture was stirred for 4 hours. The solution was evaporated under high vacuum. The residue was extracted three times with 200 ml of ethyl acetate, washed with 100 ml of cold 1N HCl and twice with 50 ml of water. The organic phases were anhydrified with anhydrous sodium sulfate, gathered, and evaporated under vacuum. The residue was dissolved in 30 ml of water and eluted with water from a column containing 30 ml of Dowex 50x8 resin, pyridinium form. The eluate was lyophilized and the residue was solubilized in 100 ml of anhydrous pyridine. 1.15 g (10 mM) of N-hydroxysuccinimide and 4.13 g (20 mM) of N,N'-dicyclohexylcarbodiimide were added at −10° C. After 15 minutes, the temperature was raised to 25° C. and the mixture was stirred for 5 hours. 5.14 g (15 mM) of L-alanine-D-isoglutamine benzyl ester hydrochloride (prepared according to Le Francier and Kusumoto) were added at 25° C. The mixture was stirred overnight and then evaporated under vacuum. The obtained residue was dissolved in 60 ml of anhydrous methanol at 25° C. 100 mg of potassium terbutylate were added, and the mixture was stirred for 30 minutes. 5 ml of anhydrous Dowex 50×8 resin, H$^+$ form, were added. The solution was filtered and evaporated under vacuum, the residue was dissolved in 30 ml of water, and 10 ml of 1N NaOH were added. The solution was stirred for 15 minutes at 25° C. and eluted with water from a column containing 30 ml of Dowex 50x8 resin, H$^+$ form. The eluate was lyophilized, and purified by silica gel chromatography, using as solvent a mixture of methylene chloride/methyl alcohol/water, 60:40:9. The fractions containing the β-2-O-ethylglycoside of N-acetyl-neuraminic acid amide with L-alanine-D-isoglutamine were gathered and evaporated under vacuum. The residue was dissolved in 50 ml of water and lyophilized. Yield: 60%

Rf=0.12, chloroform/methyl alcohol/2.5N NH$_4$OH, 60:35:8;

0.10, chloroform/methyl alcohol/0.3% CaCl$_2$, 60:40:9.

EXAMPLE 19

β-2-O-ethylglycoside of N-palmitoylneuraminic acid amide with L-alanine-D-isoglutamine 5.56 g (10 mM) of the β-2-O-ethylglycoside of N-palmitoylneuraminic acid, sodium salt, were solubilized in 50 ml of anhydrous N,N'-dimethylformamide at 25° C.; 3.06 g (11 mM) of p-bromophenacyl bromide were added and the solution was stirred overnight. 18 ml of anhydrous pyridine and 10.2 g of acetic anhydride were added and stirring was conducted for 24 hours at 35° C. The solution was evaporated under vacuum and the residue was dissolved with 100 ml of water and extracted three times with 200 ml of methylene chloride. The organic phases were washed twice with 50 ml of water and then gathered, anhydrified with anhydrous sodium sulfate and evaporated under vacuum. The obtained residue was solubilized in 50 ml of anhydrous N,N'-dimethylformamide at 25° C.; 2.64 g (20 mM) of sodium thiophenate were added and the mixture was stirred for 4 hours. The solution was evaporated under high vacuum. The residue was extracted three times with 200 ml of ethyl acetate, washed with 100 ml of cold 1N HCl and twice with 50 ml of water. The organic phases were anhydrified with anhydrous sodium sulfate, gathered, and evaporated under vacuum. The residue was dissolved in 30 ml of water and eluted with water from a column containing 30 ml of Dowex 50x8 resin, pyridinium form. The eluate was lyophilized and the residue was solubilized in 100 ml of anhydrous pyridine. 1.15 g (10 mM) of N-hydroxysuccinimide and 4.13 g (20 mM) of N,N'-dicyclohexylcarbodiimide were added at −10° C. After 15 minutes, the temperature was raised to 25° C. and the mixture was stirred for 5 hours. 5.14 g (15 mM) of L-alanine-D-isoglutamine benzyl ester hydrochloride (prepared according to Le Francier and Kusumoto) were added at 25° C. The mixture was stirred overnight and then evaporated under vacuum. The obtained residue was dissolved in 60 ml of anhydrous methanol at 25° C., 100 mg of potassium terbutylate were added, and the mixture was stirred for 30 minutes. 5 ml of anhydrous Dowex 50x8 resin, $H^+$ form, were added. The solution was filtered and evaporated under vacuum. The residue was dissolved in 30 ml of water, and 10 ml of 1N NaOH were added. The solution was stirred for 15 minutes at 25° C. and eluted with water from a column containing 30 ml of Dowex 50x8 resin, $H^+$ form. The eluate was lyophilized, and purified by silica gel chromatography, using as solvent a mixture of methylene chloride/methyl alcohol/water, 60:40:9. The fractions containing the β-2-O-ethylglycoside of N-palmitoyl-neuraminic acid amide with L-alanine-D-isoglutamine were gathered and evaporated under vacuum. The residue was dissolved in 50 ml of a mixture of water/dioxane, 4:1, and lyophilized. Yield: 60%.

Rf=0.12, chloroform/methyl alcohol/2.5N $NH_4OH$, 110:40:6.

0.57, chloroform/methyl alcohol/0.3% $CaCl_2$, 60:40:9.

EXAMPLE 20

α-2-O-ethylglycoside of N-acetylneuraminic acid amide with arginine 3.65 g (10 mM) of the α-2-O-ethylglycoside of N-acetylneuraminic acid ethyl ester, prepared according to van der Vlengel et al., Carbohydr. Res. 102, 121 (1982), were solubilized in 40 ml of water and 10 ml (10 mM) of NaOH were added. The solution was maintained at 25° C. for 30 minutes, neutralized with 1N HCl, and eluted with water from a column containing 30 ml of Dowex 50x8 resin, pyridinium form. The eluate was lyophilized and the residue was solubilized in 100 ml of anhydrous pyridine. 1.15 g (10 mM) of N-hydroxysuccinimide and 4.13 g (20 mM) of N,N'-dicyclohexylcarbodiimide were added at −10° C. After 15 minutes, the temperature was raised to 25° C. and the mixture was stirred for 5 hours. 4.64 g (15mM) of N-nitro-L-arginine benzyl ester (prepared according to Bonnaud, Bull. Chim. Farm. 121, 1982) were added at 25° C. The mixture was stirred overnight and then evaporated under vacuum. The obtained residue was dissolved in 200 ml of a mixture of n-butanol/water/acetic acid, 4:1:1, and hydrogenated in an $H_2$ current in the presence of $BaSO_4$-supported palladium. After filtration, the solution was evaporated, and the residue was purified by silica gel chromatography, using as solvent a mixture of methylene chloride/methyl alcohol/water, 60:40:9. The fractions containing the α-2-O-ethylglycoside of N-acetyl-neuraminic acid amide with arginine were gathered and evaporated under vacuum. The residue was dissolved in 50 ml of water and lyophilized. Yield: 50%.

Rf=0.13, chloroform/methyl alcohol/0.3% $CaCl_2$, 60:40:9.

EXAMPLE 21

β-2-O-ethylglycoside of N-acetylneuraminic acid amide with arginine 3.59 g (10 mM) of the β-2-O-ethylglycoside of N-acetylneuraminic acid, sodium salt, were solubilized in 50 ml of anhydrous N,N'-dimethylformamide at 25° C.; 3.06 g (11 mM) of p-bromophenacyl bromide were added and the solution was stirred overnight. 18 ml of anhydrous pyridine and 10.2 g of acetic anhydride were added and stirring was conducted for 24 hours at 35° C. The solution was evaporated under vacuum and the residue was dissolved with 100 ml of water and extracted three times with 200 ml of methylene chloride. The organic phases were washed twice with 50 ml of water and then gathered, anhydrified with anhydrous sodium sulfate, and evaporated under vacuum. The obtained residue was solubilized in 50 ml of anhydrous N,N'-dimethylformamide at 25° C.; 2.64 g (20 mM) of sodium thiophenate were added and the mixture was stirred for 4 hours. The solution was evaporated under high vacuum. The residue was extracted three times with 200 ml of ethyl acetate, washed with 100 ml of cold 1N HCl and twice with 50 ml of water. The organic phases were anhydrified with anhydrous sodium sulfate, gathered, and evaporated under vacuum. The residue was solubilized in 100 ml of anhydrous pyridine; 1.15 g (10 mM) of N-hydroxysuccinimide, 4.13 g (20 mM) of N,N'-dicyclohexylcarbodiimide and 11.6 g (10 mM) of pyridinium chloride were added at −10° C. After 15 minutes, the temperature was raised to 25° C. and the mixture was stirred for 5 hours. 4.64 g (15 mM) of N-nitro-L-arginine benzyl ester hydrochloride (prepared according to Bonnaud, Bull. Chim. Farm. 121, 1982) were added at 25° C. The mixture was stirred overnight and then evaporated under vacuum. The obtained residue was dissolved in 60 ml of anhydrous methanol at 25° C. 100 mg of potassium terbutylate were added, and the mixture was stirred for 30 minutes. 5 ml of anhydrous Dowex 50x8 resin, $H^+$ form, were added. The solution was filtered and evaporated under vacuum, and the residue was dissolved in 100 ml of a mixture of N-butanol/water/acetic acid, 4:1:1, and hydrogenated in an $H_2$ current in the presence of $BaSO_4$-supported palladium. After filtration, the solution was evaporated, and the residue was purified by silica gel chromatography, using as solvent a mixture of methylene chloride/methyl alcohol/water, 110:40:6. The fractions containing the β-2-O-ethylglycoside of N-palmitoyl-neuraminic acid amide with arginine were gathered and evaporated under vacuum. The residue was dissolved in 50 ml of water and lyophilized. Yield: 50%.

Rf=0.10, chloroform/methyl alcohol/0.3% $CaCl_2$, 60:40:9.

EXAMPLE 22

β-2-O-ethylglycoside of N-palmitoylneuraminic acid amide with arginine 5.56 g (10 mM) of the β-2-O-ethylglycoside of N-palmitoyl-neuraminic acid, sodium salt, were solubilized in 50 ml of anhydrous N,N'-dimethylformamide at 25° C.; 3.06 g (11 mM) of p-bromophenacyl bromide were added and the solution was stirred overnight. 18 ml of anhydrous pyridine and 10.2 g of acetic anhydride were added and stirring was conducted for 24 hours at 35° C. The solution was evaporated under vacuum and the residue was dissolved with 100 ml of water and extracted three times with 200 ml of methylene chloride. The organic phases were washed twice with 50 ml of water and then gathered, anhydrified with anhydrous sodium sulfate, and evaporated under vacuum. The obtained residue was solubilized in 50 ml of anhydrous N,N'-dimethylformamide at 25° C.; 2.64 g (20 mM) of sodium thiophenate were added and the mixture was stirred for 4 hours. The solution was evaporated under high vacuum. The residue was extracted three times with 200 ml of ethyl acetate, washed with 100 ml of cold 1N HCl and twice with 50 ml of water. The organic phases were anhydrified with anhydrous sodium sulfate, gathered, and evaporated under vacuum. The residue was dissolved in 30 ml of water and eluted with water from a column containing 30 ml of a Dowex 50x8 Dowex resin, pyridinium form. The eluate was lyophilized and then solubilized in 100 ml of anhydrous pyridine; 1.15 g (10 mM) of N-hydroxysuccinimide, 4.13 g (20 mM) of N,N'-dicyclohexylcarbodiimide and 11.6 g (10 mM) of pyridinium chloride were added at −10° C. After 15 minutes, the temperature was raised to 25° C. and the mixture was stirred for 5 hours. 4.64 g (15 mM) of N-nitro-L-arginine benzyl ester hydrochloride (prepared according to Bonnaud, Bull. Chim. Farm. 121, 1982) were added at 25° C. The mixture was stirred overnight and then evaporated under vacuum. The obtained residue was dissolved in 60 ml of anhydrous methanol at 25° C. 100 mg of potassium terbutylate were added, and the mixture was stirred for 30 minutes. 5 ml of anhydrous Dowex 50x8 resin, $H^+$ form, were added. The solution was filtered and evaporated under vacuum. The residue was dissolved in 100 ml of a mixture of n-butanol/water/acetic acid, 4:1:1, and hydrogenated in an $H_2$ current in the presence of $BaSO_4$-supported palladium. After filtration, the solution was evaporated, and the residue was purified by silica gel chromatography, using as solvent a mixture of methylene chloride/methyl alcohol/1.5M acetic acid, 110:40:6. The fractions containing the β-2-O-ethylglycoside of N-palmitoyl-neuraminic acid amide with arginine were gathered and evaporated under vacuum. The residue was crystallized from a mixture of 100 ml of methanol and 300 ml of ethyl ether. Yield: 60%.

Rf=0.12, chloroform/methyl alcohol/$H_2O$, 110:40:6.

EXAMPLE 23

α-2-O-ethylglycoside Of N-palmitoyl-neuraminic acid amide with arginine 5.56 g (10 mM) of the α-2-O-ethylglycoside of N-palmitoyl-neuraminic acid, sodium salt, were solubilized in 40 ml of water and eluted with water from a column containing 30 ml of 50x8 Dowex resin, pyridinium form. The eluate was lyophilized and then solubilized in 100 ml of anhydrous pyridine. 1.15 g (10 mM) of N-hydroxysuccinimide, 4.13 g (20 mM) of N,N'-dicyclohexylcarbodiimide, and 11.6 g (10 mM) of pyridinium chloride were added at −10° C. After 15 minutes, the temperature was raised to 25° C. and the mixture was stirred for 5 hours. 4.64 g (15 mM) of N-nitro-L-arginine benzyl ester hydrochloride (prepared according to Bonnaud, Bull. Chim. Farm. 121, 1982) were added at 25° C. The mixture was stirred overnight and then evaporated under vacuum. The residue was dissolved in 100 ml of a mixture of n-butanol/water/acetic acid, 4:1:1, and hydrogenated in an $H_2$ current in the presence of $BaSO_4$-supported palladium. After filtration, the solution was evaporated, and the residue was purified by silica gel chromatography, using as solvent a mixture of methylene chloride/methyl alcohol/1.5M acetic acid, 110:40:6. The fractions containing the α-2-O-ethylglycoside of N-palmitoyl-neuraminic acid amide with arginine were gathered and evaporated under vacuum. The residue was crystallized from a mixture of 40 ml of methanol and 150 ml of ethyl ether. Yield: 70%.

Rf=0.14, chloroform/methyl alcohol/$H_2O$, 110:40:6;

0.32, chloroform/methyl alcohol/2.5N $NH_4OH$, 60:35:8.

EXAMPLE 24

Dimethylamide of N-palmitoylneuraminic acid 5.34 g (10 mM) of the α-2-O-ethylglycoside of N-palmitoyl-neuraminic acid were suspended in a mixture of 100 ml of 0.1M $H_2SO_4$/ethanol, 4:1, at 60° C., and stirred for 16 hours. The product was extracted once with 100 ml of ethyl acetate. The organic phases were washed three times with 50 ml of water, gathered, and evaporated under vacuum. The obtained residue was dissolved in 200 ml of anhydrous methanol at 25° C. 20 ml of anhydrous Dowex 50x8 resin, $H^+$ form, were added. The mixture was stirred for 2 hours. To the filtered solution, 4.5 g (100 mM) of dimethylamine were added at 25° C. and the solution was stirred for 24 hours. The mixture was evaporated, and the residue was purified by silica gel chromatography, using as solvent a mixture of methylene chloride/methyl alcohol/water, 80:20:2. The fractions containing the dimethylamide of N-acetyl-neuraminic acid were gathered and evaporated under vacuum. The residue was dissolved in 60 ml of a mixture of water/dioxane, 4:1, and lyophilized. Yield: 75%.

Rf=0.63, chloroform/methyl alcohol/$H_2O$, 110:40:6.

EXAMPLE 25

β-2-ethylglycoside morpholino-propylamide of N-palmitoylneuraminic acid 5.62 g (10 mM) of β-2-ethylglycoside N-palmitoylneuraminic acid ethyl ester were solubilized in 50 ml of anhydrous methanol; 14.4 g (100 mM) of N-(3-aminopropyl)-morpholine were added. The mixture was stirred overnight at 25° C. The solution was evaporated under vacuum and the residue was purified by silica gel chromatography, using as solvent a mixture of methylene chloride/methyl alcohol/water, 80:10:1. The fractions containing the compound were gathered and evaporated under vacuum. The residue was dissolved in 100 ml of water and lyophilized. Yield: 85%.

Rf=0.30, chloroform/methyl alcohol/$H_2O$, 80:20:2;

0.62, chloroform/methyl alcohol/2.5N $NH_4OH$, 110:40:6.

EXAMPLE 26

β-2-ethylglycoside morpholino-propylamide of N-palmitoylneuraminic acid (maleic acid salt)

5.56 g (10 mM) of β-2-O-ethylglycoside N-palmitoylneuraminic acid ethyl ester were solubilized in 50 ml of pyridine; 2.3 g (20 mM) of pyridinium chloride and 4.12 g (20 mM) of N,N'-dicyclohexylcarbodiimide were added. The mixture was stirred for 2 hours at 25° C. 14.4 g (100 mM) of N-(3-aminopropyl)-morpholine were added. The mixture was stirred overnight at 25° C. The solution was evaporated under vacuum and the residue was purified by silica gel chromatography, using as solvent a mixture of methylene chloride/methyl alcohol/water, 80:10:1. The fractions containing the β-2-ethylglycoside morpholino-propylamide of N-palmitoylneuraminic acid were gathered and evaporated under vacuum. The residue was dissolved in 100 ml of water. After adding a stoichiometric amount of maleic acid, the mixture was lyophilized. Yield: 85%.

Rf=0.30, chloroform/methyl alcohol/$H_2O$, 80:20:2;

0.62, chloroform/methyl alcohol/2.5N $NH_4OH$, 110:40:6.

EXAMPLE 27

Dimethylaminopropylamide of N-palmitoyl-neuraminic acid 5.34 g (10 mM) of the α-2-O-ethylglycoside of N-palmitoyl-neuraminic acid were suspended in a mixture of 100 ml of 0.1M $H_2SO_4$/ethanol, 4:1, at 60° C., and stirred for 16 hours. The product was extracted once with 200 ml of ethyl acetate and then twice with 100 ml of ethyl acetate; the organic phases were washed three times with 50 ml of water, gathered, and evaporated under vacuum. The obtained residue was dissolved in 200 ml of anhydrous methanol at 25° C. 20 ml of anhydrous Dowex 50x8 resin, $H^+$ form, were added. The mixture was stirred for 2 hours. To the filtered solution 10.2 g (100 mM) of dimethyl-aminopropylamine were added at 25 C. and the solution was stirred for 24 hours. The mixture was evaporated, and the residue was purified by silica gel chromatography, using as solvent a mixture of methylene chloride/methyl alcohol/2.5N $NH_4OH$, 60:35:8. The fractions containing the compound were gathered and evaporated under vacuum. The residue was dissolved in 60 ml of a mixture of water/dioxane, 1:2, and lyophilized. Yield: 70%.

Rf=0.21, chloroform/methyl alcohol/0.3% $CaCl_2$, 60:40:9.

EXAMPLE 28

Dimethylaminopropylamide of N-palmitoyl-neuraminic acid (maleic acid salt)

5.34 g (10 mM) of the α-2-O-ethylglycoside of N-palmitoyl-neuraminic acid were suspended in a mixture of 100 ml of 0.1M $H_2SO_4$/ethanol, 4:1, at 60° C., and stirred for 16 hours. The product was extracted once with 200 ml of ethyl acetate and then twice with 100 ml of ethyl acetate; the organic phases were washed three times with 50 ml of water, gathered, and evaporated under vacuum. The obtained residue was dissolved in 200 ml of anhydrous methanol at 25° C. 20 ml of anhydrous Dowex 50x8 resin, $H^+$ form, were added. The mixture was stirred for 2 hours. To the filtered solution 10.2 g (100 mM) of dimethyl-aminopropylamine were added at 25° C., and the solution was stirred for 24 hours. The mixture was evaporated, and the residue was purified by silica gel chromatography, using as solvent a mixture of methylene chloride/methyl alcohol/2.5N $NH_4OH$, 60:35:8. The fractions containing the compound were gathered and evaporated under vacuum. The residue was dissolved in 60 ml of a mixture of water/dioxane, 1:2. A stoichiometric amount of maleic acid was added, and the mixture was lyophilized. Yield: 70%.

Rf=0.21, chloroform/methyl alcohol/0.3% $CaCl_2$, 60:40:9.

EXAMPLE 29

β-2-O-ethylglycoside butylamide of N-palmitoylneuraminic acid 5.62 g (10 mM) of β-2-O-ethylglycoside N-palmitoylneuraminic acid ethyl ester were solubilized in 50 ml of anhydrous methanol; 3.66 g (50 mM) of 2-butylamine were added. The mixture was stirred for 5 hours at 40° C. The solution was evaporated under vacuum and the residue was purified by silica gel chromatography, using as solvent a mixture of methylene chloride/methyl alcohol/water, 80:10:1. The fractions containing the β-2-O-ethylglycoside butylamide of N-palmitoylneuraminic acid were gathered and evaporated under vacuum. The residue was dissolved in 60 ml of dioxane and lyophilized. Yield: 70%.

Rf=0.71, chloroform/methyl alcohol, 80:20;

0.60, chloroform/methyl alcohol/2.5N $NH_4OH$, 80:20:2.

EXAMPLE 30

β-2-O-ethylglycoside dimethylaminoethylamide of N-palmitoylneuraminic acid 5.62 g (10 mM) of β-2-O-ethylglycoside N-palmitoylneuraminic acid ethyl ester were solubilized in 50 ml of anhydrous methanol; 4.4 g (50 mM) of 2-dimethylaminoethylamine were added. The mixture was stirred overnight at 40° C. The solution was evaporated under vacuum and the residue was purified by silica gel chromatography, using as solvent a mixture of methylene chloride/methyl alcohol/2.5N $NH_4OH$, 80:20:2. The fractions containing the β-2-O-ethylglycoside dimethylaminoethylamide of N-palmitoylneuraminic acid were gathered and evaporated under vacuum. The residue was dissolved in 60 ml of water and lyophilized. Yield: 80%.

Rf=0.11, chloroform/methyl alcohol, 70:30;

0.43, chloroform/methyl alcohol/2.5N $NH_4OH$, 110:40:6.

EXAMPLE 31

β-2-O-ethlglycoside dimethylaminoethylamide of N-palmitoylneuraminic acid (maleic acid salt)

5.56 g (10 mM) of β-2-O-ethylglycoside N-palmitoylneuraminic acid were solubilized in 50 ml of pyridine; 2.3 g (20 mM) of pyridinium chloride and 4.12 g (20 mM) of N,N'-dicyclo-hexylcarbodiimide were added. The mixture was stirred for 2 hours at 25° C. 8.8 g (100 mM) of dimethylaminoethylamine were added and the reaction was conducted overnight at 25° C. The solution was evaporated under vacuum and the residue was purified by silica gel chromatography, using as solvent a mixture of methylene chloride/methyl alcohol/2.5N $NH_4OH$, 80:20:2. The fractions containing the β-2-O-ethylglycoside dimethylaminoethylamide of N-palmitoylneuraminic acid were gathered and evaporated under vacuum. The residue was dissolved in 60 ml of water. A stoichiometric amount of maleic acid was added, and the mixture was lyophilized. Yield: 80%.

Rf=0.11, chloroform/methyl alcohol, 70:30;

0.43, chloroform/methyl alcohol/2.5N $NH_4OH$, 110:40:6.

EXAMPLE 32

β-2-ethylglycoside dimethylaminopropylamide of N-dichloroacetyl neuraminic acid 4.34 g (10 mM) of β-2-O-ethylglycoside N-dichloroacetylneuraminic acid ethyl ester were solubilized in 50 ml of anhydrous methanol; 10.2 g (100 mM) of dimethylaminopropylamine were added. The mixture was stirred for 5 hours at 40° C. The solution was evaporated under vacuum and the residue was purified by silica gel chromatography, using as solvent a mixture of methylene chloride/methyl alcohol/water, 40:60:15. The fractions containing the β-2-O-ethylglycoside dimethyl-aminopropylamide of N-dichloroacetylneuraminic acid were gathered and evaporated under vacuum. The residue was dissolved in 60 ml of water and lyophilized. Yield: 65%.

Rf=0.37, chloroform/methyl alcohol/2.5N $NH_4OH$, 40:60:15.

EXAMPLE 33

β-2-O-ethylglycoside dimethylaminopropylamide of N-dichloroacetylneuraminic acid (maleic acid salt)

4.34 g (10 mM) of the β-2-O-ethylglycoside of N-dichloro-acetylneuraminic acid ethyl ester were solubilized in 50 ml of anhydrous methanol; 10.2 g (100 mM) of dimethylamino-propylamine were added. The mixture was stirred for 5 hours at 40° C. The solution was evaporated under vacuum and the residue was purified by silica gel chromatography, using as solvent a mixture of methylene chloride/methyl alcohol/water, 40:60:15. The fractions containing the β-2-O-ethylglycoside dimethyl-aminopropylamide of N-dichloroacetylneuraminic acid were gathered and evaporated under vacuum. The residue was dissolved in 60 ml of water. A stoichiometric amount of maleic acid was added, and the mixture was lyophilized. Yield: 65%.

Rf=0.37, chloroform/methyl alcohol/2.5N $NH_4OH$, 40:60:15.

EXAMPLE 34

β-2-O-ethylglycoside dimethylaminopropylamide of neuraminic acid 3.23 g (10 mM) of the β-2-O-ethylglycoside of neuraminic acid ethyl ester, prepared according to Schauer and Buscher, Biochim. Biophys. Acta 338, 369 (1974), were solubilized in 50 ml of anhydrous methanol; 10.2 g (100 mM) of dimethylamino-propylamine were added. The mixture was stirred overnight at 40° C. The solution was evaporated under vacuum and the residue was purified by reverse phase chromatography, using as support Lichroprep RP 18 (Merck, Darmstadt, Germany) and as eluant a mixture of methyl alcohol/water, 1:1. The fractions containing the β-2-O-ethylglycoside dimethyl-aminopropylamide of neuraminic acid were gathered and evaporated under vacuum. The residue was dissolved in 50 ml of water and lyophilized. Yield: 60%.

Rf=0.1, chloroform/methyl alcohol/0.3% $CaCl_2$, 55:45:10.

EXAMPLE 35

β-2-O-ethylglycoside dimethylamide of N-dichloroacetylneuraminic acid 4.34 g (10 mM) of the β-2-O-ethylglycoside of N-dichloro-acetylneuraminic acid ethyl ester were solubilized in 50 ml of anhydrous methanol; 4.5 g (100 mM) of dimethylamine were added. The mixture was stirred overnight at 40° C. The solution was evaporated under vacuum and the residue was purified by silica gel chromatography, using as solvent a mixture of methylene chloride/methyl alcohol/water, 80:10:1. The fractions containing the β-2-O-ethylglycoside dimethyl-amide of N-dichloroacetylneuraminic acid were gathered and evaporated under vacuum. The residue was crystallized from 60 ml of methanol and 300 ml of ethyl ether. Yield: 60%.

Rf=0.44, chloroform/methyl alcohol/2.5N $NH_4OH$, 110:40:6.

EXAMPLE 36

α-2-O-ethylglycoside ethanolamide of N-palmitoyl-neuraminic acid 5.48 g (10 mM) of the α-2-O-ethylglycoside of N-palmitoylneuraminic acid ethyl ester were solubilized in 50 ml of anhydrous methanol; 6.11 g (100 mM) of ethanolamine were added. The mixture was stirred overnight at 35° C. The solution was evaporated under vacuum and the residue was purified by silica gel chromatography, using as solvent a mixture of methylene chloride/methyl alcohol, 90:10. The fractions containing the α-2-O-ethylglycoside ethanolamide of N-palmitoyl-neuraminic acid were gathered and evaporated under vacuum. The residue was dissolved in 60 ml of dioxane/water, 2:1, and lyophilized. Yield: 85%.

Rf=0.66, chloroform/methyl alcohol/$H_2O$, 110:40:6.

EXAMPLE 37

β-2-O-ethylglycoside dimethylamide of neuraminic acid 3.23 g (10 mM) of the β-2-O-ethylglycoside of neuraminic acid ethyl ester were solubilized in 50 ml of water and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/2.5N $NH_4OH$, 110:40:6. The fractions containing the β-2-O-ethylglycoside dimethylamide of neuraminic acid were gathered and evaporated under vacuum. The residue was dissolved in 50 ml of water and lyophilized. Yield: 55%.

Rf=0.30, chloroform/methyl alcohol/$H_2O$, 55:45:10.

EXAMPLE 38

β-2-O-ethylglycoside dimethylamide of N-caprylneuraminic acid 3.23 g (10 mM) of the β-2-O-ethylglycoside of neuraminic acid ethyl ester were solubilized at 5° C. in 100 ml anhydrous methanol and 50 ml of anhydrous methylene chloride. 8.25 g (40 mM) of N,N'-dicyclohexylcarbodiimide, 2.0 g (20 mM) of triethylamine, and 3.44 g (20 mM) of capric acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/ $H_2O$, 80:10:1. The fractions containing the β-2-O-ethylglycoside dimethylamide of N-caprylneuraminic acid were gathered and evaporated under vacuum. The residue was dissolved in 50 ml of acetone and precipitated in 20 volumes of n-hexane. Yield: 65%.

Rf=0.48, chloroform/methyl alcohol/$H_2O$, 80:10:1.

EXAMPLE 39

β-2-O-ethylglycoside dimethylamide of N-capryloyl-neuraminic acid 3.23 g (10 mM) of the β-2-O-ethylglycoside of neuraminic acid ethyl ester were solubilized at 5° C. in 100 ml anhydrous methanol and 50 ml of anhydrous methylene chloride. 8.25 g (40 mM) of N,N'-dicyclohexylcarbodiimide, 2.0 g (20 mM) of triethylamine, and 2.88 g (20 mM) of caprylic acid were added and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/ $H_2O$, 80:10:1. The fractions containing the β-2-O-ethylglycoside dimethylamide of N-caproyloylneuraminic acid were gathered and evaporated under vacuum. The residue was dissolved in 50 ml of acetone and precipitated in 20 volumes of n-hexane. Yield: 65%.

Rf=0.61, chloroform/methyl alcohol/$H_2O$, 80:20:2.

EXAMPLE 40

β-2-O-ethylglycoside dimethylamide of N-oleylneuraminic acid 3.23 g (10 mM) of the β-2-O-ethylglycoside of neuraminic acid ethylester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 5.65 g (20 mM) of oleic acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol, 9:1. The fractions containing the β-2-O-ethylglycoside dimethylamide of N-oleylneuraminic acid were gathered and evaporated under vacuum. The residue was dissolved in 50 ml of tert-butanol and lyophilized. Yield: 50%.

Rf=0.42, chloroform/methyl alcohol/$H_2O$, 80:20:2.

EXAMPLE 41

β-2-O-ethylglycoside dimethylamide of N-valproyl-neuraminic acid 3.23 g (10 mM) of the β-2-O-ethylglycoside of neuraminic acid ethylester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 2.88 g (20 mM) of valproic acid were added and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/ $H_2O$, 80:10:1. The fractions containing the β-2-O-ethylglycoside dimethylamide of N-valproylneuraminic acid were gathered and evaporated under vacuum. The residue was dissolved in 50 ml of acetone and precipitated in 20 volumes of n-hexane. Yield: 50%.

Rf=0.60, chloroform/methyl alcohol/$H_2O$, 80:20:2.

EXAMPLE 42

β-2-O-ethylglycoside dimethylamide of N-phenylacetyl-neuraminic acid 3.23 g (10 mM) of the β-2-O-ethylglycoside of neuraminic acid ethyl ester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 2.72 g (20 mM) of phenylacetic acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added, and the reaction was conducted overnight at 25° C. The solution was evaporated, and the residue was purified by silica gel chromatography, using as solvent a mixture of methylene chloride/methyl alcohol/ $H_2O$, 80:10:1. The fractions containing the β-2-O-ethylglycoside dimethylamide of N-phenylacetylneuraminic acid were gathered and evaporated under vacuum. The residue was dissolved in 50 ml of acetone and precipitated in 20 volumes of n-hexane. Yield: 65%.

Rf=0.43, chloroform/methyl alcohol/$H_2O$, 80:20:2.

EXAMPLE 43

β-2-O-ethylglycoside dimethylamide of N-miristoyl-neuraminic acid 3.23 g (10 mM) of the β-2-O-ethylglycoside of neuraminic acid ethyl ester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 4.57 g (20 mM) of miristic acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/$H_2O$, 80:10:1. The fractions containing the β-2-O-ethylglycoside dimethylamide of N-miristoylneuraminic acid were gathered and evaporated under vacuum. The residue was dissolved in 50 ml of acetone and precipitated in 20 volumes of n-hexane. Yield: 60%.

Rf=0.56, chloroform/methyl alcohol/$H_2O$, 80:20:2.

EXAMPLE 44

β-2-O-ethylglycoside dimethylamide of N-lauroyl-neuraminic acid 3.23 g (10 mM) of the β-2-O-ethylglycoside of neuraminic acid ethyl ester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 4.57 g (20 mM) of lauric acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/$H_2O$, 80:10:1. The fractions containing the β-2-O-ethylglycoside dimethylamide of N-palmitoylneuraminic acid were gathered and evaporated under vacuum. The residue was dissolved in 50 ml of acetone and precipitated in 20 volumes of n-hexane. Yield: 60%.

Rf=0.54, chloroform/methyl alcohol/$H_2O$, 80:20:2.

EXAMPLE 45

β-2-O-ethylglycoside dimethylamide of N-nicotinoyl-neuraminic acid 3.23 g (10 mM) of the β-2-O-ethylglycoside of neuraminic acid ethyl ester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 2.46 g (20 mM) of nicotinic acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/$H_2O$, 80:10:1. The fractions containing the β-2-O-ethylglycoside dimethylamide of N-nicotinoylneuraminic acid were gathered and evaporated under vacuum. The residue was dissolved in 50 ml of methanol and precipitated in 20 volumes of tert-butyl-ether. Yield: 50%.

Rf=0.27, chloroform/methyl alcohol/$H_2O$, 80:20:2.

EXAMPLE 46

β-2-O-ethylglycoside dimethylamide of N-trimethoxy-benzoylneuraminic acid 3.23 g (10 mM) of the β-2-O-ethylglycoside of neuraminic acid ethyl ester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 4.24 g (20 mM) of trimethoxybenzoic acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 4.5 g (100 mM) of diethylamine were added and the reaction was conducted overnight at 25° C. The solution was evaporated, and the residue was purified by silica gel chromatography, using as solvent a mixture of methylene chloride/methyl alcohol/$H_2O$, 80:10:1. The fractions containing the β-2-O-ethylglycoside dimethylamide of N-trimethoxbenzoylneuraminic acid were gathered and evaporated under vacuum. The residue was dissolved in 50 ml of methanol and precipitated in 20 volumes of tert-butyl-ether. Yield: 60%.

Rf=0.52, chloroform/methyl alcohol/$H_2O$, 80:20:2.

EXAMPLE 47

β-2-O-ethylglycoside pyrrolidylamide of N-palmitoyl-neuraminic acid 5.56 g (10 mM) of the β-2-O-ethylglycoside of N-palmitoylneuraminic acid, sodium salt, were solubilized in 50 ml of anhydrous pyridine. 2.3 g (20 mM) of pyridinium chloride and 4.12 g (20 mM) of N,N'-dicyclohexylcarbodiimide were added. The mixture was stirred for 2 hours at 25° C. 7.17 g (100 mM) of pyrrolidine were added and the reaction was conducted overnight at 25° C. The solution was evaporated, and the residue was purified by silica gel chromatography, using as solvent a mixture of methylene chloride/methyl alcohol, 9:1. The fractions containing the β-2-O-ethylglycoside pyrrolidylamide of N-palmitoylneuraminic acid were gathered and evaporated under vacuum. The residue was dissolved in 50 ml of acetone and precipitated in 20 volumes of n-hexane. Yield: 90%.

Rf=0.67, chloroform/methyl alcohol/$H_2O$, 80:20:2.

EXAMPLE 48

β-2-O-ethylglycoside of N-palmitoylneuraminic acid ethyl ester 3.23 g (10 mM) of the β-2-O-ethylglycoside of neuraminic acid ethyl ester were solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 5.12 g (20 mM) of palmitic acid were added, and the mixture was stirred overnight at 5° C. After filtration, it was evaporated. The residue was solubilized in 100 ml of ethanol/water, 1:1, and 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. The residue was solubilized in 150 ml of water and the product was extracted once with 300 ml chloroform and then twice with 150 ml of chloroform; the organic phases were washed three times with 150 ml of water, gathered, and evaporated. The residue was purified by silica gel chromatography, using as solvent a mixture of methylene chloride/methyl alcohol, 9:1. The fractions containing the β-2-O-ethylglycoside of N-palmitoylneuraminic acid were gathered and evaporated under vacuum. The residue was crystallized from 100 ml of tert-butyl-ether. Yield: 85%.

Rf=0.44, methylene chloride/methanol, 90:10.

EXAMPLE 49

β-2-O-ethylglycoside of N-palmitoylneuraminic acid 5.65 g (10 mM) of the β-2-O-ethylglycoside of neuraminic acid ethyl ester were solubilized in 100 ml of ethanol/water, 1:1. 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. Yield: 95%.

Rf=0.14, methylene chloride/methyl alcohol/$H_2O$, 110:10:6.

EXAMPLE 50

α-2-O-ethylglycoside of N-palmitoyl-neuraminic acid methyl ester 3.37 g (10 mM) of the α-2-O-ethylglycoside of neuraminic acid methyl ester were solubilized in 30 ml of 1M NaOH at 80° C., and maintained under stirring overnight. The solution was passed through a column containing 200 ml of Bio-Rex 70 H+ weakly basic resin, and then dessicated under vacuum. The residue was redissolved with 50 ml of anhydrous methanol. 4.13 g (20 mM) of N,N'-dicyclohexylcarbodiimide and 2.3 g of pyridinium chloride were added, and the mixture was stirred for 1 hour. After filtration, it was evaporated. The residue was solubilized at 5° C. in 100 ml of anhydrous methanol and 50 ml of anhydrous methylene chloride. 8.25 g (40 mM) of N,N'-dicyclohexylcarbodiimide, 2.0 g (20 mM) of triethylamine, and 5.12 g (20 mM) of palmitic acid were added, and the mixture was stirred overnight at 5° C. After filtration, it was evaporated. The residue was solubilized in 150 ml of water and the product was extracted once with 300 ml chloroform and then twice with 150 ml of chloroform; the organic phases were washed three times with 150 ml of water, gathered, and evaporated. The residue was purified by silica gel chromatography, using as solvent a mixture of methylene chloride/methyl alcohol, 9:1. The fractions containing the α-2-O-ethylglycoside of N-palmitoylneuraminic methyl ester were gathered and evaporated under vacuum. The residue was crystallized from 100 ml of tert-butyl-ether. Yield: 70%.

Rf=0.65, methylene chloride/methanol, 90:10.

EXAMPLE 51

α-2-O-ethylglycoside of N-palmitoylneuraminic acid, sodium salt 5.47 g (10 mM) of the α-2-O-ethylglycoside of neuraminic acid methyl ester were solubilized in 100 ml of methanol/water, 1:1. 11 ml (10 mM) of 1M NaOH were added. The solution was maintained at 25° C. for 30 minutes. 2 ml of anhydrous Dowex 50x8 resin, $H^+$ form, were added. The filtered solution was evaporated under vacuum. Yield: 95%.

Rf=0.25, chloroform/methyl alcohol/$H_2O$, 110:10:6.

EXAMPLE 52

β-2-O-ethylglycoside of N-dichloroacetylneuraminic acid ethyl ester 3.23 g (10 mM) of the β-2-O-ethylglycoside of neuraminic acid ethyl ester were solubilized in 50 ml of anhydrous pyridine at 25° C.; 14.3 g (100 mM) of methyl dichloroacetate were added. The mixture was stirred for 24 hours and then evaporated under vacuum. The residue was purified by silica gel chromatography, using as solvent a mixture of methylene chloride/methyl alcohol/$H_2O$, 80:10:1. The fractions containing the β-2-O-ethylglycoside of N-dichloroacetylneuraminic ethyl ester were gathered and evaporated under vacuum. The residue was crystallized from a mixture of 50 ml of methanol and 200 ml of ethyl ether. Yield: 85%.

Rf=0.49, chloroform/methanol, 80:20.

Biological Studies

The antineuronotoxic activities of the new amides of the neuraminic acids of the present invention are demonstrated by the following experimental studies conducted with the β-2-O-ethylglycoside of the dimethylamide of N-palmitoylneuraminic acid of the formula:

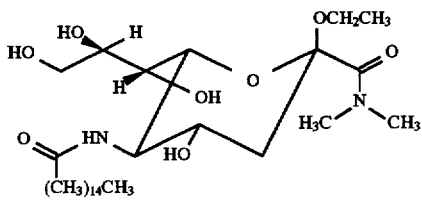

identified as ND37.

EXAMPLE 53

Antineuronotoxic effect of ND37 in vitro on cerebellar granule cells: protective effect on exogenous glutamate induced neurotoxicity

Materials and Methods

Cell Cultures

Primary cell cultures of cerebellar granule Cells were prepared from 6 day old Sprague-Dawley rats. Neurons were grown in 35 mm plates for 11–13 days and maintained in a humid environment (95% air and 5% $CO_2$). Cultures ($3 \times 10^6$ cells/plate) are mainly formed by granule cells (95%) with a small amount (5%) of glial cells (Gallo V. et al.: Selective release of glutamate from cerebellar granule cells differentiating in culture. Proc. Natl. Acad. Sci. USA 79, 7919–23, 1982). Glial proliferation was prevented by arabinofuranoside cytosine.

Derivative ND37 was solubilized at a concentration of $1 \times 10^{-2}$M in dimethylsulfoxide (1% DMSO) and then diluted at various concentrations in Locke's solution (154 mM NaCl/1/5.6 mM KCl/3.6 mM $NaHCO_3$/2.3 mM $CaCl_2$/1 mM $MgCl_2$/5.6 mM glucose/5 mM HEPES, pH 7.4). The following concentrations were tested: $5 \times 10^{-6}$M, $1 \times 10^{-5}$M, and $2 \times 10^{-5}$M.

Description of the Exogenous Glutamate Neurotoxicity Model

The cell culture medium was aspirated from the plates (and correctly maintained). Plates were washed ($3 \times 2$ ml) with Locke's solution, and solutions (1.5 ml) containing the compound to be tested (concentrations from $5 \times 10^{-6}$M to $2 \times 10^{-5}$M) were added and incubated for 2 hours in an incubator at 37° C. (5% $CO_2$).

Treated cells were washed ($3 \times 2$ ml) with Locke's solution+10% fetal calf serum, then washed ($3 \times 2$ ml) with Locke's solution without $Mg^{++}$. 100 µM glutamate (1.5 ml) in Locke's solution ($-Mg^{++}$) or culture medium (controls) were added. Incubation with glutamate was performed for 15 minutes at room temperature (27° C.). Glutamate was removed, the plates were washed with Locke's solution ($2 \times 2$ ml), and then incubated in presence of the starting medium (correctly maintained) for 24 hours at 37° C. in an incubator (5% $C_2O$). At the end of the incubation, cellular viability was assayed via quantification by the MTT colorimetric test (Mosmann T.: Rapid colorimetric assay for cellular growth and survival: application to proliferation and cytotoxicity assays. J. Immunol. Meth. 65, 55: 63, 1983 and modified according to Skaper S. D. et al.: Death of cultured hippocampal pyramidal neurons induced by pathological activation of N-methyl-D-aspartate receptors is reduced by monosialogangliosides. J. Pharm. Exp. Ter. 259,1 452–457, 1991). Data are expressed as % survival. The significance was calculated according to the Dunnett test.

Results

The obtained results (Table 1) show that:

ND37 has a marked antineuronotoxic activity: the presence of the free compound in the incubation medium during the exposure to the glutamate toxin is not necessary. The neuroprotective effect of ND37 is very high: at a concentration of $1 \times 10^{-5}$M there is a protection of about 63%, and the highest protection (about 83%) is reached at a concentration of $2 \times 10^{-5}$M.

TABLE 1

Antineuronotoxic effect of ND37 in cerebellar granule cells: protective effect on exogenous glutamate induced neurotoxicity

| Groups | | MTT values | % survival |
|---|---|---|---|
| 1) control | | 0.195 ± 0.016 | 100 |
| 2) glutamate | | 0.075 ± 0.009 | 38 ± 5 |
| 3) glutamate + ND37 | ($5 \times 10^{-6}$ M) | 0.110 ± 0.015 | 37 ± 5 |
| | ($1 \times 10^{-5}$ M) | 0.123 ± 0.006* | 63 ± 3 |
| | ($2 \times 10^{-5}$ M) | 0.326 ± 0.016* | 83 ± 6 |

Significance (Dunnett's test)
*p < 0.01 (vs group 2)

EXAMPLE 54

Antineuronotoxic effect of ND37 in vitro in cerebellar granule cells: protective effect on exogenous glutamate-induced neurotoxicity during cotreatment of cells with the active compound

Materials and Methods

Cell Cultures

Primary cerebellar granule cells were prepared from 8 day old rats (Zivic Miller, Pittsburgh, Pa, USA). Neurons were cultivated in 35 mm plates for 7–8 days and maintained in a humid environment (95% air and 5% $CO_2$). Cultures ($3 \times 10^6$ cells/plate) are mainly formed by granule cells (95%) with a small amount (5%) of glial cells (Gallo V. et al.: Selective release of glutamate from cerebellar granule cells differentiating in culture. Proc. Natl. Acad. Sci. USA 79, 7919–23, 1982). Glial proliferation was prevented by arabinofuranoside cytosine.

Derivative ND37 was solubilized at a concentration of $1 \times 10^{-2}$M in dimethylsulfoxide (1% DMSO), and then diluted at various concentrations in Locke's solution (154 mM NaCl/5.6 mM KCl/3.6 mM $NaHCO_3$/2.3 mM $CaCl_2$/1 mM $MgCl_2$/5.6 mM glucose/5 mM HEPES, pH 7.4). The following concentrations were tested: $5 \times 10^{-6}$M, $1 \times 10^{-5}$M, and $2 \times 10^5$M.

Description of the Exogenous Glutamate Neurotoxicity model

The cell culture medium was aspirated from the plates (and correctly maintained). Plates were washed ($3 \times 2$ ml) with Locke's solution without $Mg^{++}$, and solutions (1.5 ml) containing the compound to be tested (concentrations from $5 \times 10^6$M to $2 \times 10^5$M) were added and incubated for 2 hours in an incubator at 37° C. (5% $CO_2$).

Treated cells were washed ($3 \times 2$ ml) with Locke's solution+10% fetal calf serum, then washed ($3 \times 2$ ml) with Locke's solution without $Mg^{++}$. 1.5 ml of Locke's solution ($-Mg^{++}$) or 50 µM of glutamate±the test compound (concentrations between 1 and $4 \times 10^{-5}$M) in 1.5 ml of Locke's solution ($-M^{++}$) were added. The incubation was conducted for 15 minutes (37° C.). Glutamate and the compound were removed. The plates were washed with Locke's solution (2×2 ml), and then incubated in the presence of the starting medium (correctly maintained) for 24 hours at 37° C. in an incubator (5% $CO_2$). At the end of the incubation, cellular viability was assayed via quantification by the fluorescein diacetate (FDA) and propidium iodide (PI) colorimetric test (Manev H. et al.: Glutamate induced neuronal death in primary cultures of cerebellar granule cells: protection by synthetic derivatives of endogenous sphingolipids; J. Pharm. Exp. Ther. 252,1 419–427, 1990). Monolayers were washed with Locke's solution and stained for 3 minutes at 22° C. with a solution containing 36 µM FDA and 7 µM of PI. The stained cells where immediately analyzed using a standard fluorescence microscope for epi-illumination (Vanox Olympus, 450 nm excitation, 520 nm emission). FDA, a non polar ester, crosses cell membranes and is hydrolyzed by intracellular esterases with the consequent production of a yellow greenish color. Neuronal damage influences the FDA-induced color and allows the permeation of PI, which is a polar compound capable of interacting with nuclear DNA, producing a brilliant red fluorescence.

After glutamate treatment, some neurons can degenerate and detach from the plates. The loss of cells was estimated by comparing the number of intact or degenerated neurons in a well defined field, which was photographed before and after 24 hours after application of glutamate. The percent of surviving neurons in 4 representative fields (magnification 40×) of each monolayer was determined by a researcher unaware of the experimental conditions, evaluating the FDA/PI color, and calculating it as follows:

$$\frac{\text{FDA positive cells}}{\text{FDA positive + PI positive + loosened cells}} \times 100$$

Data are expressed as % of surviving cells. Significance was calculated using the Dunnett's test.

Results

The data in Table 2 show that the neuroprotective effect of ND37 on glutamate toxicity is immediate, i.e., ND37 protects neurons at a dose of 10–40 µM, even if administered contemporaneously with the application of the toxin. This shows the rapid mode of action of ND37.

TABLE 2

Antineuronotoxic effect of ND37 during cotreatment of exogenous glutamate on cerebellar granule cells (protective effect)

| Groups | | % surviving cells N = 4 (average + s.e.) FDA/PI test |
|---|---|---|
| 1) control | | 89 ± 7.0 |
| 2) glutamte | | 22 ± 1.5 |
| 3) glutamate + ND37 | (1 × 10⁻⁵ M) | 34 ± 2.0 |
| | (2 × 10⁻⁵ M) | 70 ± 6.0* |
| | (4 × 10⁻⁵ M) | 88 ± 4.5 |

Significance (Dunnett's test)
*p < 0.01 (vs group 2)

EXAMPLE 55

In vivo effect of ND37 on cerebral damage induced by intracerebroventricular (icv) injection of N-methyl-D-aspartate in neonatal rats Materials and Methods Description of the Model Experiments were performed on 7 day old neonatal rats weighing ca. 13 grams. At the 7th day, animals, after ether anesthesia, were lesioned by icv injection of 25 nmoles/µl of N-methyl-D-aspartate (NMDA), Sigma, St. Louis, Mo, USA, according to the method described by McDonald et al. (McDonald J. W. et al.: Neurotoxicity of N-methyl-D-aspartate is markedly enhanced in developing rat central nervous system. Brain Res. 459, 200–203, 1988). The excitotoxin was solubilized in saline, and the pH was brought to 7.4 by adding 1N NaOH. The NMDA injection (25 nmoles/µl) was performed slowly (2 minutes) at the level of the right lateral ventricle utilizing a Hamilton syringe. Saline was administered to control animals (1 µl icv).

The compound was administered subcutaneously (sc) after suspension in 1% DMSO (experiment No. 1) or in 0.5% tragacanth (experiment No. 2). The compound was tested at the following doses: 1-3-5 mg/kg sc.

The treatment was conducted performing two administrations:

1 hour before NMDA injection;

immediately after NMDA injection.

Experimental Groups 1. (n=8) saline (1 µl)+saline (1 µl)
2. (n=14) NMDA (25 nmoles µl)+saline (1 µl)
3. (n=15) NMDA (25 nmoles µl)+ND37 (1 mg/kg/ml)
4. (n=15) NMDA (25 nmoles µl)+ND37 (3 mg/kg/ml)
5. (n=15) NMDA (25 nmoles µl)+ND37 (5 mg/kg/ml)

The number of animals utilized in each experimental group (corresponding to the total number of animals, i.e., experiment 1+experiment 2, according to Table 3) is indicated in brackets.

Parameters

Animals were sacrificed on the 12th day (i.e., 5 days after NMDA injection) for the evaluation of the in toto brain weight, defined in mg.

The statistical significance was evaluated using Dunnett's test.

Results

The obtained results (Table 3) show that:

treatment with ND37 is effective in reducing the brain damage induced by the excitotoxin (evaluated as the lowering of total brain weight;

ND37 is significatively effective (p<0.01) at a dose of 1 mg/kg sc.

TABLE 3

Antineurotoxic effect of ND37 in vivo: evaluation of the protection of cerebral damage (total brain weight) induced by NMDA in neonatal rat

| Groups | Compounds | Doses (mg/kg) | Total brain weight (mg) |
|---|---|---|---|
| Experiment n.1 (vehicle = DMSO 1%) | | | |
| 1. (n = 4) control + saline | | | 1017 |
| 2. (n = 7) NMDA + saline | | | 841 |
| 3. (n = 8) NMDA + ND 37 | | 1 | 960* |
| 4. (n = 8) NMDA + ND 37 | | 3 | 968* |
| 5. (n = 8) NMDA + ND 37 | | 5 | 959* |

TABLE 3-continued

Antineurotoxic effect of ND37 in vivo: evaluation of the protection of cerebral damage (total brain weight) induced by NMDA in neonatal rat

| Groups | Compounds | Doses (mg/kg) | Total brain weight (mg) |
|---|---|---|---|
| Experiment n.2 | | | |
| 1. (n = 4) | control + saline | | 1017 |
| 2. (n = 7) | NMDA + saline | | >841 |
| 3. (n = 7) | NMDA + ND 37 | 1 | 1019 |
| 4. (n = 7) | NMDA + ND 37 | 3 | 977* |
| 5. (n = 7) | NMDA + ND 37 | 5 | 976* |

*p < 0.01 vs lesioned not treated (group 2)
(In all experiments the standard deviation is less than 5%).
In brackets is the indication of the number of animals.
Compounds under examination were administered at doses of 1-3-5 mg/kg sc 1 hours before NMDA injection (25 nmoles/1 ul) and immediately after NMDA. Brain weight is expressed in mg.

Modulatory in vitro effect of ND37 on release and/ or uptake of excititatory negrotransmitter in cerebellar granule cells: determination of glutamate and aspartate content in potassium induced depolarization Materials and Methods Cell cultures Primary cell cultures of cerebellar granule cells were prepared from 8 day old Sprague-Dawley rats.

Neurons were grown in 35 mm plates for 11–13 days and maintained in a humid environment (95% air and 5% $CO_2$). Cultures ($3 \times 10^6$ cells/plate) are mainly formed by granule cells (95%, with a small amount (5%) of glial cells (Gallo V. et al.: Selective release of glutamate from cerebellar granule cells differentiating in culture. Proc. Natl. Acad. Sci. USA 79, 7919–23, 1982). Glial proliferation was prevented by arabinofuranoside cytosine.

Derivative ND37 was solubilized at a concentration of 10M in dimethylsulfoxide (1% DMSO), and then diluted at various concentrations (0.1-1-10-20 µM) in Locke's solution (154 mM NaCl/5.6 mM KCl/3.6 mM $NaHCO_3$/2.3 mM $CaCl_2$/1 mM $MgCl_2$/5.6mM glucose/5 mM HEPES, pH 7.4).

Description of Exogenous Glutamate Neurotoxicity Model

The cell culture medium was aspirated from the plates. Plates were washed (3×2 ml) with Locke's solution, and solutions (750 µl) containing the compound to be tested (concentrations from 0.1 to 20 µM) were added and incubated for 2 hours in an incubator at 37° C. (5% $CO_2$) both in the presence and absence of different depolarizing concentrations of KCl (between 5 and 50 mM). The incubation medium was gathered, filtered through a 0.2 µ filter, and processed (220 µl) for the analysis of the amino acid content.

Parameters

The glutamate and aspartate content (expressed as µM) was evaluated by HPLC (high pressure liquid chromatography), according to Bidlingmeryer B. A. et al., J. Chromatogr. 336, 93–104, 1984.

Results

The obtained results show that ND37 is able to diminish in cerebellar granule cells, in a dose-dependent manner (Table 4), the potassium-induced increase of glutamate and aspartate (Table 5). The compound, administered at doses up to 20 µM, did not modify the basal levels (controls) of extracellular glutamate and aspartate (Table 5), whereas it reduced by ca. 30% the extracellular glutamate induced by KCl potassium already at a dose of 0.1 µM (Table 4). ND 37 completely abolished the glutamate increase induced by KCl in the culture medium at a dose of 20 µM (Table 5).

20 µM ND73 completely abolished the extracellular increase of glutamate and aspartate induced by KCl (15, 25, 30, and 50 mM). The extracellular values for glutamate and aspartate in cultures exposed to KCl in the presence of ND37 were between 0.01 and 0.28% of the values obtained without the compound (Table 5).

The possible mechanism of action of ND37 may reside in the release and/or uptake of endogenous compounds.

TABLE 4

Dose dependent inhibitory action of ND37 (0.1 - 1 - 10 - 20 uM) on extracellular glutamate increase induced by KCl in primary cerebellar granule cells.

| Groups | Extracellular glutamate content (uM) | % KCl 50 Mm |
|---|---|---|
| 1) controls | 0.04 ± 00 | |
| 2) KCl (50 mM) | 17.40 ± 0.19 | 100 |
| 3) KCl (50 mM) + ND37 (0.1 uM) | 12.60 ± 0.57 | 72 |
| 4) KCl (50 mM) + ND37 (1 uM) | 13.30 ± 1.33 | 76 |
| 5) KCl (50 mM) + ND37 (10 uM) | 5.60 ± 2.37* | 32 |
| 6) KCl (50 mM) + ND37 (20 uM) | 0.11 ± 0.09* | 0.01 |

Triplicate experiments (mean + s.e.)
*p < 0.01 vs. group 2 (Dunnett's test)

TABLE 5

Effect of ND37 (20 uM) on extracellular glutamate and aspartate content in cerebellar granule cells in depolarizing conditions induced by different concentrations of KCl (15–50 mM).

| Groups | Extracell. glutamate content (uM) | % corresp. KCl | Extracell. aspartate content (uM) | % corresp. KCl |
|---|---|---|---|---|
| 1) controls | 0.354 | | 0.020 | |
| 2) controls + ND 37 (20 uM) | 0.362 | | 0.039 | |
| 3) KCl (30 mM) | 23.115 | 100 | 1.016 | 100 |
| KCl (50 mM) + ND37 (20 uM) | 0.318* | 0.01 | 0.063 | 0.06 |
| 4) KCl (50 mM) | 10.863 | 100 | 0.621 | 100 |
| KCl (50 mM) + ND37 (20 uM) | 0.246* | 0.02 | 0.078 | 0.13 |
| 5) KCl (25 mM) | 5.195 | 100 | 0.386 | 100 |
| KCl (50 mM) + ND37 (20 uM) | 0.330* | 0.06 | 0.107 | 0.28 |
| 6) KCl (15 mM) | 2.454 | 100 | 0.484 | 100 |
| KCl (50 mM) + ND37 (20 uM) | 0.899* | 0.34 | 0.046 | 0.09 |

Triplicate experiments
*p < 0.01 (Dunnet's test) vs corresponding group only treated with KCl (in all experiments standard deviation less than 5%)

EXAMPLE 56

Electrophysiological characterization of neurons treated with ND37: absence of an effect on glutamate-stimulated cationic channels Materials and Methods Primary cell cultures of cerebellar granule cells were prepared from 8 day old rats (Zivic Miller, Pittsburgh, Pa, USA).

Neurons were grown on 35 mm plates for 7–8 days and maintained in a humid environment (95% air and 5% $CO_2$). Cultures ($2.5\times10^6$ cells/plate) were mainly formed by granule cells (95%), with a small amount (5%) of glial cells (Gallo V. et al.: Selective release of glutamate from cerebellar granule cells differentiating in culture. Proc. Natl. Acad. Sci. USA 79, 7919–23, 1982). Glial proliferation was prevented by arabinofuranoside cytosine.

Primary cell cultures of cortical neurons were prepared from one day old neonatal mice (Zivic Miller, Pittsburgh, Pa., USA) (Bertolino and Vicini: Mol. Pharmacol. 34, 98–103, 1988).

Cultures were grown on 35 mm plates, to which was added 10 μg/ml of poly-L-lysine, at a density of $5\times10^5$ cortical neurons/plate. Cultures were prepared on basal Eagle medium (Gibco) containing 10% fetal calf serum (Gibco), 25 mM KCl, 2 mM glutamine, and 100 μg/ml gentamycine. Glial proliferation was prevented by adding 1 μM arabinofuranoside cytosine 24 hours after seeding. Cortical neurons were cultivated for 3 weeks.

Derivative ND37 was solubilized at a concentration of $1\times10^{-2}$M in dimethylsulfoxide (1% DMSO), and then diluted at various concentrations in Locke's solution ($-Mg^{++}$) (154 mM NaCl/5.6 mM KCl/3.6 mM $NaHCO_3$/2.3 mM $CaCl_2$/5.6 mM glucose/5 mM HEPES, pH 7.4). ND37 was analyzed at concentrations of 20 and 30 μM.

Description of electrophysiological measurements of glutamate-related cationic channel activity cerebellar granule neurons and cortical neurons culture Experiments were performed at room temperature utilizing the following medium 145 mM NaCl, 1 mM $CaCl_2$, 5 mM glucose, and 5 mM HEPES/NaOH at pH 7.4, and patch pipettes, close to the preparation, containing 145 mM $CsCl_2$, 1 mM $CaCl_2$, 11 mM ethyleneglycol (β-aminoethyl ether) bis N,N'-tetraacetic acid, 10 mM HEPES/Cs(OH)$_2$ at pH 7.2. Plates were continually perfused at a flow rate of 1 ml/min.

a) "Sealed" registrations on whole cells (Hamill O. P et al., "Improved patch-clamp techniques for high-resolution current recording from cells and cell-free membranes patches", Pfluegers Arch. 391, 85–100, 1981) were performed on cerebellar granule cells or cortical neurons from neonatal rats and grown in cultures for 1 or 2 weeks, respectively.

Glutamate was released under pressure (2–6 psi) from glass micropipettes (with tips having a greater delivery capacity than that, 4–6 μM, of patch pipettes) on the cell bodies of voltage clamped neurons (maintenance voltage—40 mV).

b) The activation by glutamate of single channels was externally recorded on membrane portions prepared from cerebellar granule cells pretreated with ND37 for 30 minutes at 37° C. Micropipettes, filled (1 μM) with glutamate, were positioned close to the membrane portions and were also utilized in order to drip the neurotransmitter. Single channel currents were registered according to the method described by Bertolini and Vicini ("Voltage-dependent block by strychnine of N-methyl-D-aspartic acid-activated cationic channels in rat cortical neurons in culture", Mol. Pharmacol. 34, 98–103, 1988).

Registration on the whole cell

Glutamate (50 μM), able to activate currents directed inside, was released by pressure on voltage-clamped cell bodies of cerebellar and cortical neurons. Because these experiments were performed in the absence of $Mg^{++}$, the response to glutamate was probably mediated by the NMDA and non-NMDA glutamate receptor. The combined administration of ND37 (30 μM) and glutamate (50 μM), does not influence the control response, which is not different from the controls (mean 200 pA at voltage—50 mV) in the three different conditions in 3 cerebellar and 5 cortical preparations.

Results

In order to evaluate the activities of ND37 on glutamate response, 10 different experiments were performed. In cerebellar granule cell membrane preparations, high conductivity, glutamate-activated (50 pS) cationic channels are prevalent. Pretreatment of cells for 30 minutes with 20 μM ND37 does not influence the channel conductivity and the frequency of their opening (Table 6). According to the single channel registration, no kinetic and conductivity variations were observed after ND37 treatment. The inside currents activated by glutamate (50 μM) given contemporaneously with ND37 (30 μM) were not different from those activated only by glutamate.

TABLE 6

Effect of ND37 on glutamate controlled cationic channels activity in cerebellar granule neurons and cortical neurons in culture.

| Group n = 10 | Single channel current registration (cerebellar granule neurons) | |
|---|---|---|
| | Channel conductivity (ps) | Opening frequence (opening/sec) |
| 1) Glutamate (1 mM) | 50 | 4.5 ± 2.9 |
| 2) Glutamate + ND37 (20 uM) | 50 | 4.1 ± 2.1 |

Conclusions

ND37, a compound protecting neurons from glutamate receptor-mediated toxicity, does not seem to produce this effect blocking the ionotropic glutamate receptors, as can be seen from the absence of effects of cationic glutamate stimulated channels.

EXAMPLE 57

The neuritogenic activity of the new compounds of the present invention can be shown by experiments performed with the aforesaid compound ND37, and with the 2-ethylglycoside of N-palmitoyl-neuraminic acid dimethylaminopropylamide, which will be subsequently referred to as ND35.

Materials and Methods

Cell Cultures

C1300 mouse neuroblastoma cells, Neuro-2a clone, (American Cell Type Culture Collection, Bethesda, Md.) were grown at a density of 10,000 cells/well in a culture medium containing Dulbecco's modified Eagle medium (DMEM, Flow), 10% fetal calf serum (FCS, batch IP 02, Seromed), penicillin (100 units per ml, Irvine), and L-glutamine (2 mM, Sigma). Cells were incubated at 37° C. for 24 hours, and medium was removed and substituted with 350 μl of fresh medium plus compounds to be tested.

Tested Compounds and Their Solubilization

Compounds ND35 and ND37 were solubilized at a concentration of $1\times10^{-2}$M in dimethylsulfoxide (1% DMSO).

For the different compounds, progressive dilutions in culture medium were performed (concentrations from $1\times10^{-5}$ to $1\times10^{-4}$M).

Parameters

Neuritogenic activity (cell number with neurites, optical microscopy)

Culture plates were incubated with compounds to be tested and analyzed using a phase contrast microscope (250×). Nine fields with prefixed coordinates were chosen and photographed. Then the total number of cells and those with neurites (length at least double the cell diameter) were counted in blind in each photograph. The percentage of cells with neurites was determined after counting of at least 100 cells (Facci L. et al.: Promotion of neuritogenesis in mouse neuroblastoma cells by exogenous ganglioside GM1. J. Neurochem. Raven Press, New York, 299–305,1984).

Results

The obtained results (Table 7) show that derivatives ND35 and ND37 both induce neuritogenesis in vitro. In particular, under the tested experimental conditions, it was shown that:

the neuritogenic effect was already significant at a concentration of $5\times10^{-5}$M ($p<0.01$), with the highest efficacy (about 48% of cells with neurites) at a concentration of $1\times10^{-4}$M.

TABLE 7

Neuritogenic effect of ND35 and ND37 in N2a neuroblastoma cells.

| Compounds (concentrations) | | Cells with neurites (%) |
|---|---|---|
| Control | | 2 ± 3 |
| ND37 | ($1 \times 10^{-4}$) | 48 ± 9* |
|  | ($5 \times 10^{-5}$) | 27 ± 5* |
|  | ($2.5 \times 10^{-5}$) | 8 ± 4 |
|  | ($1 \times 10^{-5}$) | 5 ± 3 |
| ND35 | ($1 \times 10^{-4}$) | 39 ± 7* |
|  | ($5 \times 10^{-5}$) | 28 ± 7* |
|  | ($2.5 \times 10^{-5}$) | 7 ± 3 |
|  | ($1 \times 10^{-5}$) | 7 ± 2 |

*$p < 0.01$ vs. control (Dunnett's test)

CONCLUSIONS

The foregoing results show a good pharmacological profile of the compounds according to the present invention. Their antineuronotoxic and modulatory effects on extracellular levels of excititatory neurotransmitter amino acids should be noted in particular.

Owing to their antineuronotoxic activity, the new derivatives of neuraminic acid can be used in pathologies related to the excitotoxic effect of excititatory amino acids. It has been shown that these amino acids, e.g., glutamic acid and aspartic acid, besides their important functions in several physiological processes such as, for example, synaptogenesis and plasticity, are involved in the ethiogenesis and/or evolution of different pathologies related to neuronal evolution and/or death. Although neuronal damage can have several causes, neuronal dysfunctions excite a cascade of cellular events, such as the activation of $Ca^{++}$ ion-dependent enzymes, the influx of $Ca^{++}$ ions, and the activation of second messengers, which cause neuronal death. Damage to the nervous system due to excititatory amino acids is present in ischaemia, hypoxia, epilepsy, trauma, compressions, metabolic disfunctions, aging, and toxic-infective and chronic neurodegenerative diseases, like Alzheimer's and Huntington's diseases.

Because of the modulatory effect of the new derivatives on the processes of release and/or uptake, and of the increase in the intracellular space, of neurotransmitter amino acids, these new compounds have therapeutic relevance in neuropsychiatric disorders, where the pathological event derives from the imbalance of the aforesaid processes. Owing to the fact that the protective action of the derivatives of invention against the toxicity of excititatory amino acids occurs through the activation of glutamate receptors, the use of these compounds does not have the disadvantages of other known derivatives, which block these receptors (see Olney J. W. et al.: "Pathological changes induced in cerebrocortical neurons by phencyclidine and related drugs", Science 224, 1360–1362, 1989; Olney J. W. et al.: "NMDA antagonist neurotoxicity: mechanism and prevention, Science 254, 1515–1518, 1991).

Finally, the new compounds of the present invention, because of their neuritogenic activity, are valuable in therapies related to the recovery of nervous functions in pathologies associated with neuronal damage, like peripheral neuropathies.

PHARMACEUTICAL APPLICATIONS OF THE COMPOUNDS OF THE PRESENT INVENTION

Objects of the present invention also include pharmaceutical preparations having, as active ingredients, one or more of the new aforesaid derivatives and, particularly, those especially mentioned or those described in the foregoing examples.

These pharmaceutical preparations can used for oral, rectal, parenteral, local or intradermic use. They can therefore be in solid or semisolid form, e.g., pills, tablets, gelatineous soft capsules, capsules, soft gelatin suppositories, etc. For parenteral use, it is possible to use formulations for intramuscular, subcutaneous, or transdermic use, or suitable for infusions or intravenous injections, and they can therefore be prepared as solutions of active components or as a lyophilized powder of the active components, eventually to be added to one or more excipients or pharmaceutically acceptable solvents, which are usable for the aforesaid purpose, and which are osmolar with physiological fluids. For local application, spray preparations, e.g,. nasal sprays, can be employed, or ointments for topical use, or plasters for transdermal administration can be used.

The preparations of the present invention can be used both in man and animals. Preferably, they contain between about 0.01% and 10% of the active components for solutions, sprays, ointments and creams, and between 1% and 100%, preferably between 5% and 50% of the active component, for solid form preparations.

The dosage will vary according to the indication, the desired effect, and the route of administration. For therapeutic administration, or for prophylaxis by the parenteral route, the dosage varies preferentially between 0.05 and 10 mg per kg body weight per day, and especially between 0.05 and 2 mg per kg body weight per day.

The invention being thus described, it will be obvious that the same may be varied in many ways. Such variations are not to be regarded as a departure from the spirirt and scope of the invention, and all such modifications as would be obvious to one skilled in the art are intended to be included within the scope of the following claims.

We claim:
1. A compound selected from the group consisting of
(a) a carboxylic amide of a compound of formula I:

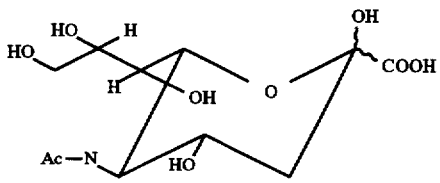

wherein C-1 is amidated, and
wherein Ac represents an acyl residue of an aliphatic, araliphatic, aromatic, alicyclic or heterocyclic carboxylic acid, having at least 10 but not more than 24 carbons,
(b) a 2-hydrocarbyl-glycoside of said amide,
(c) a peracylated derivative of said amide, or of the 2-hydrocarbyl glycoside of said amide wherein all to the hydroxyl groups of formula I are acylated and the amide substituent on C-2 is in the α position,
(d) a basic addition salt of one of the foregoing compounds, and
(e) an acidic addition salt of one of the foregoing compounds having an acidic or basic function.

2. A carboxylic amide according to claim 1, wherein said acyl group Ac is an acyl residue of a substituted or non-substituted acid, said substituted acid having from one to three substituents selected from the group consisting of a halogen atom, a free, esterified, or etherified hydroxylic or mercapto group, a free or esterified carboxylic or sulfonic group, a free or esterified carboxylic or sulfonic group transformed into an amide, a free or amino group-substituted hydrocarbylic group, and a hydrocarbylic group interrupted by an —SO—, —SO$_2$—, or phenylene group.

3. A carboxylic amide according to claim 2, wherein said halogen atom is a member selected from the group consisting of fluorine, chlorine and bromine.

4. A carboxylic amide according to claim 2, wherein said esterified hydroxylic or mercapto group is the esterified form of an aliphatic or aromatic acid which acid has not more than 8 carbon atoms.

5. A carboxylic amide according to claim 2, wherein said etherified hydroxy or mercapto group, or said esterified carboxylic or sulfonic group, is the etherified or esterified form of an aliphatic alcohol, which aliphatic alcohol, has not more than 8 carbon atoms, or of an araliphatic alcohol, which araliphatic alcohol has one benzene ring and an alkylene of 1 or 2 carbon atoms.

6. A carboxylic amide according to claim 2, wherein hydrocarbylic group which substitutes said amino group is an alkyl with at least 8 carbon atoms or an aralkyl with one benzene ring and an alkylene of 1 or 2 carbon atoms.

7. A carboxylic amide according to claim 2, wherein said acyl group Ac is saturated.

8. A carboxylic amide according to claim 1, wherein said acyl group Ac is unsaturated and contains only one double bond.

9. A carboxylic amide according to claim 1, wherein said acyl group Ac is the acyl residue of an acid selected from the group consisting of capric, undecilic, di-tert-butyl-acetic, lauric, tridecilic, myristic, pentadecilic, palmitic, margaric, stearic, arachic, behenic and lignoceric acid.

10. A carboxylic amide according to claim 1, wherein said acyl group Ac is the acyl residue of tryptophan.

11. A carboxylic amide according to claim 1, wherein said acyl group Ac is the acyl residue of a peptide.

12. A carboxylic amide according to claim 1, wherein said acyl group Ac is an acyl residue of trimethoxybenzoic acid or diphenyl-O,O'-dicarbonic acid.

13. A carboxylic amide according to claim 1, wherein said acyl group Ac is an acyl residue of a heterocyclic acid selected from the group consisting of cinchoninic, lysergic, isolysergic, dihydrolysergic, 2-bromo-lysergic, 2-bromo-dihydrolysergic, 1-methyl-lysergic, 1-methyl-dihydro-lysergic, and 1-methyl-2-bromo lysergic.

14. A carboxylic amide according to claim 1, wherein the amido group of the amidated C-1 carboxyl group is —CONH$_2$, or is substituted with a primary or secondary aliphatic, aromatic, araliphatic, alicyclic or heterocyclic amine having not more than 24 carbon atoms.

15. A carboxylic amide according to claim 14, wherein said amido group is substituted with one to three groups selected from the group consisting of a free, esterified or etherified hydroxylic or mercapto group; a halogen atom; a free, esterified, or amide-modified carboxylic or sulfonic group; a free amino group; and a hydrocarbyl-substituted amino group wherein said hydrocarbyl group is interrupted with an —SO— or —SO$_2$— group.

16. A carboxylic amide according to claim 15, wherein said esterified hydroxy or mercapto group is substituted with said esterified hydroxy or mercapto group is substituted with an aliphatic or aromatic acid having not more than 8 carbon atoms.

17. A carboxylic amide according to claim 15, wherein said esterified hydroxy or mercapto group, or said esterified carboxylic or sulfonic group, is substituted with an aliphatic alcohol having not more than 8 carbon atoms, or with an araliphatic alcohol having only one benzene ring and an alkylene of 1 or 2 carbon atoms.

18. A carboxylic amide according to claim 15, wherein said hydrocarbyl group substituting said amino group is an alkyl having not more than 8 carbon atoms, or an aralkyl with only one benzene ring and an alkylene of 1 or 2 carbon atoms.

19. A carboxylic amide according to claim 14, wherein said amine is an alkyl- or dialkylamine having between 1 and 12 carbon atoms.

20. A carboxylic amide according to claim 14, wherein said amine is an alkylenamine having between 3 and 6 carbon atoms constituting the ring.

21. A carboxylic amide according to claim 14, wherein the amine is methylamine, ethylamine, propylamine, hexylamine, diethylamine, dimethylamine, diisopropylamine, dihexylamine pyrrolidine, piperidine, or azepine.

22. A carboxylic amide according to claim 14, wherein the amine is an aliphatic diamine.

23. A carboxylic amide according to claim 22, wherein said diamine is selected from the group consisting of ethylenediamine, trimethylenediamine, tetramethylenediamine, pentamethylenediamine, hexamethylenediamine, piperazine, and N-alkyl or C-alkyl derivatives of said diamine having from 1 to 4 carbons in the alkyl group.

24. A carboxylic amide according to claim 14, wherein the amine is aminoethanol, aminopropanol, mercaptoethylamine, morpholine, tiomorpholine, and a C1–C4 alkyl derivative of said amine.

25. A carboxylic amide according to claim 14, wherein the amine is an amino acid selected from the group consisting of valine, leucine, phenylalanine, tryptophan, α-aminobutyric acid, β-aminobutyric acid, methionine, lysine, aspartic acid, glutamic acid, proline, and hydroxyproline.

26. A carboxylic amide according to claim 14, wherein the amine is a natural or synthetic peptide having not more than 12 carbon atoms.

27. A carboxylic amide according to claim 14, wherein the amine is a peptide.

28. A carboxylic amide according to claim 14, wherein the amine is selected from the group consisting of phosphatidylethanolamine, phosphatidylserine, sphingosine, dihydrosphingosine, psychosine, dihydropsychosine, phosphorylcholine-sphingosine, phosphorylcholine-dihydrosphingosine, and phytosphingosine.

29. A carboxylic amide according to claim 14, wherein the amine is either an aromatic amine having one aromatic ring, wherein said aromatic ring is non-substituted, or an aromatic amine substituted with one to three functional groups selected from the group consisting of halogen, hydroxy, methoxy, carboxy sulfonyl, and C1–C4 aliphatic hydrocarbylic.

30. A carboxylic amide according to claim 14, wherein the amine is a heterocyclic amine selected from the group consisting of a pyrimidine base, a purine, ephedrine, tyramine, and adrenaline.

31. A carboxylic amide according to claim 1, wherein the aglycon of the 2-hydrocarbyl-glycoside is substituted with an aliphatic alcohol having not more than 12 carbon atoms.

32. A carboxylic amide according to claim 1, wherein the aglycon of the 2-hydrocarbyl-glycoside is substituted with an araliphatic alcohol having one benzene ring, wherein said benzene ring is non-substituted, or a benzene ring substituted with 1–3 C1–C4 alkyl groups, and having not more than 4 carbon atoms in the aliphatic chain.

33. A carboxylic amide according to claim 1, wherein the aglycon of the 2-hydrocarbyl-glycoside is substituted with an alicyclic alcohol or an aliphatic-alicyclic alcohol having only one cycloaliphatic ring and not more than 14 carbon atoms.

34. A carboxylic amide according to claim 1, wherein the aglycon of the 2-hydrocarbyl-glycoside is substituted with a heterocyclic alcohol having not more than 12 carbon atoms, and only one heterocyclic ring containing 1 or 2 heteroatoms selected from the group consisting of —NH—, —O—, and —S—.

35. A carboxylic amide according to claim 1, wherein the aglycon of the 2-hydrocarbyl-glycoside is substituted with a corticosteroid steroid alcohol.

36. A carboxylic amide according to claim 1, wherein in the peracylated derivatives, the acyl groups are acyl residues of derived from aliphatic acids having not more than 10 carbon atoms.

37. A carboxylic amide according to claim 1, wherein in the peracylated derivatives, the acyl groups are acyl residues of aromatic acids having only one benzene ring.

38. A compound which is the β-2-O-ethylglycoside of N-palmitoyl-neuraminic acid.

39. A compound which is the β-2-O-ethylglycoside dimethylamide of N-palmitoyl-neuraminic acid.

40. A compound which is the β-2-O-ethylglycoside L-alanyl-D-isoglutaminylamide of N-palmitoylneuraminic acid.

41. A compound selected from the group consisting of
(a) a peracylated derivative of a carboxylic ester of the compound of the following formula:

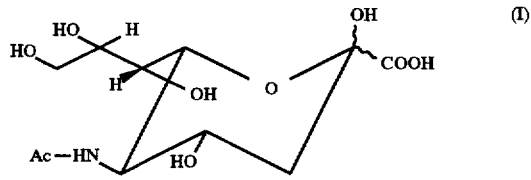

wherein C-1 is amidated, and wherein Ac represents an acyl residue of an aliphatic, araliphatic, aromatic, alicyclic, or heterocyclic carboxylic acid, and (b) a basic or acidic addition salt of said peracylated derivative.

42. A process for preparing a peracylated derivative of a carboxylic amide of N-acylneuraminic acid of claim 1 using a neuraminic acid having a free amino group as a starting material, comprising introducing in a stepwise manner, (a) the C-1 amide function, and (b) the acyl groups onto the free amino group and each of the hydroxy groups of the compound of formula I.

43. The process according to claim 42, further comprising forming a salt of said carboxylic amide.

44. The process according to claim 42, wherein the free amino group of a neuraminic acid starting material is acylated with the desired acid.

45. A process for preparing a peracylated-derivative of a carboxylic ester or salt thereof according to claim 41, comprising introducing into the compound of formula I, in a stepwise manner, (a) the ester function onto the carboxylic group and (b) the acyl groups onto each of the hydroxy groups.

46. The process according to claim 42, further comprising introducing a 2-glycosidic group into the neuraminic acid starting material.

47. The process according to claim 46, further comprising forming salts of said amide.

48. A pharmaceutical composition, comprising a compound according to claim 1 as active ingredient, and a pharmaceutically acceptable carrier.

49. A method of reducing glutamate or aspartate induced neurotoxicity comprising:

exposing cells to a compound of claim 1 at a concentration sufficient to prevent or reduce neurotoxicity induced by glutamate or aspartate-derived excititatory amino acids.

50. A method of inducing neuritogenesis comprising exposing cells to a compound of claim 1 at a concentration sufficient for inducing neuritogenesis.

* * * * *